United States Patent [19]

Mushabac

[11] Patent Number: 5,562,448
[45] Date of Patent: Oct. 8, 1996

[54] METHOD FOR FACILITATING DENTAL DIAGNOSIS AND TREATMENT

[76] Inventor: David R. Mushabac, 919 Ocean Ave., Brooklyn, N.Y. 11226

[21] Appl. No.: 743,103

[22] Filed: Aug. 9, 1991

Related U.S. Application Data

[63] Continuation-in-part of Ser. No. 507,162, Apr. 10, 1990, and a continuation-in-part of Ser. No. 694,446, May 1, 1991.

[51] Int. Cl.⁶ .................................... G06F 159/00
[52] U.S. Cl. ............................................. 433/215
[58] Field of Search ................. 364/413.2; 433/39, 433/215; 128/660

[56] References Cited

U.S. PATENT DOCUMENTS

| | | |
|---|---|---|
| 3,971,133 | 7/1976 | Mushabac . |
| 4,182,312 | 1/1980 | Mushabac . |
| 4,239,431 | 12/1980 | Davini . |
| 4,349,277 | 9/1982 | Mundy et al. . |
| 4,436,684 | 3/1984 | White . |
| 4,525,858 | 6/1985 | Cline et al. . |
| 4,564,295 | 1/1986 | Halioua . |
| 4,575,805 | 3/1986 | Moermann et al. . |
| 4,577,968 | 3/1986 | Makosch . |
| 4,611,288 | 9/1986 | Duret et al. . |
| 4,657,394 | 4/1987 | Halioua . |
| 4,663,720 | 5/1987 | Duret et al. ........................ 364/474 |
| 4,763,791 | 8/1988 | Halverson et al. . |
| 4,837,732 | 6/1989 | Brandestini et al. . |
| 4,936,862 | 6/1990 | Walker et al. . |
| 4,937,928 | 7/1990 | van der Zel ........................ 433/223 |
| 4,941,826 | 7/1990 | Loran et al. . |
| 5,092,022 | 5/1992 | Duret ............................ 364/474.05 |
| 5,142,930 | 9/1992 | Allen et al. ........................ 74/469 |

OTHER PUBLICATIONS

"Optical Methods to Measure Shape and Size" P. M. Boone *Adv. Dent. Res.* 1(1):27–38, Oct., 1987.
"Optical Methods to Measure Shape and Size" P. M. Boone (paper).

*Primary Examiner*—Gail O. Hayes
*Attorney, Agent, or Firm*—R. Neil Sudol; Henry D. Coleman

[57] ABSTRACT

A method for use in forming a preparation in a patient's jaw comprises the steps of (a) generating electrically encoded data specifying pre-existing dental structure in the patient's jaw, (b) transmitting the data to a computer, (c) operating the computer to generate, on a monitor connected to the computer, a graphic representation of the pre-existing structure, (d) further operating the computer to predetermine an optimal position and an optimal orientation of a material removal tool with respect to the pre-existing structure, and (e) additionally operating the computer to generate, on the monitor, a graphic representation of the tool in the optimal position and the optimal orientation relative to the pre-existing structure. The method may be used to conduct a practice operation on the patient. In such a practice operation, the dental practitioner orients a dental type instrument (e.g., a probe or a drill) in juxtaposition to the pre-existing structure at the optimal position (shown on the monitor). The computer is provided with electrical feedback or signals as to the actual position and the actual orientation of the instrument. The computer is then operated to automatically determine an angle between the optimal orientation and the actual orientation. The computer then alerts the dental practitioner as to the deviation, if any, between the instrument and the optimal position and orientation thereof.

42 Claims, 12 Drawing Sheets

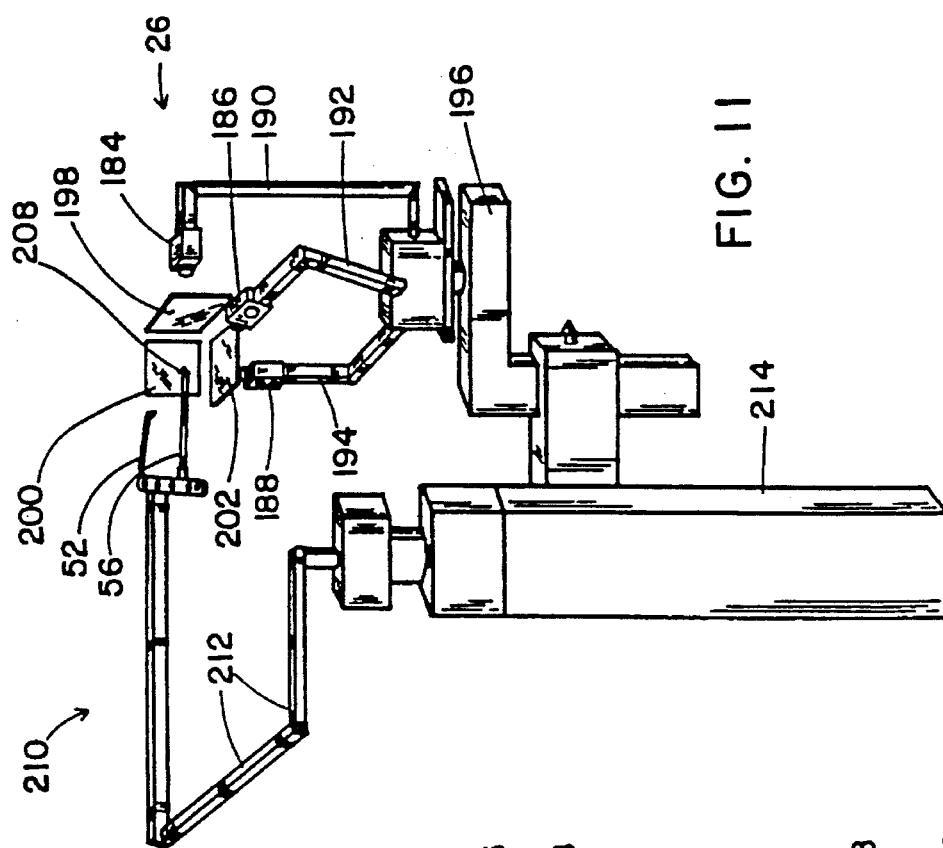
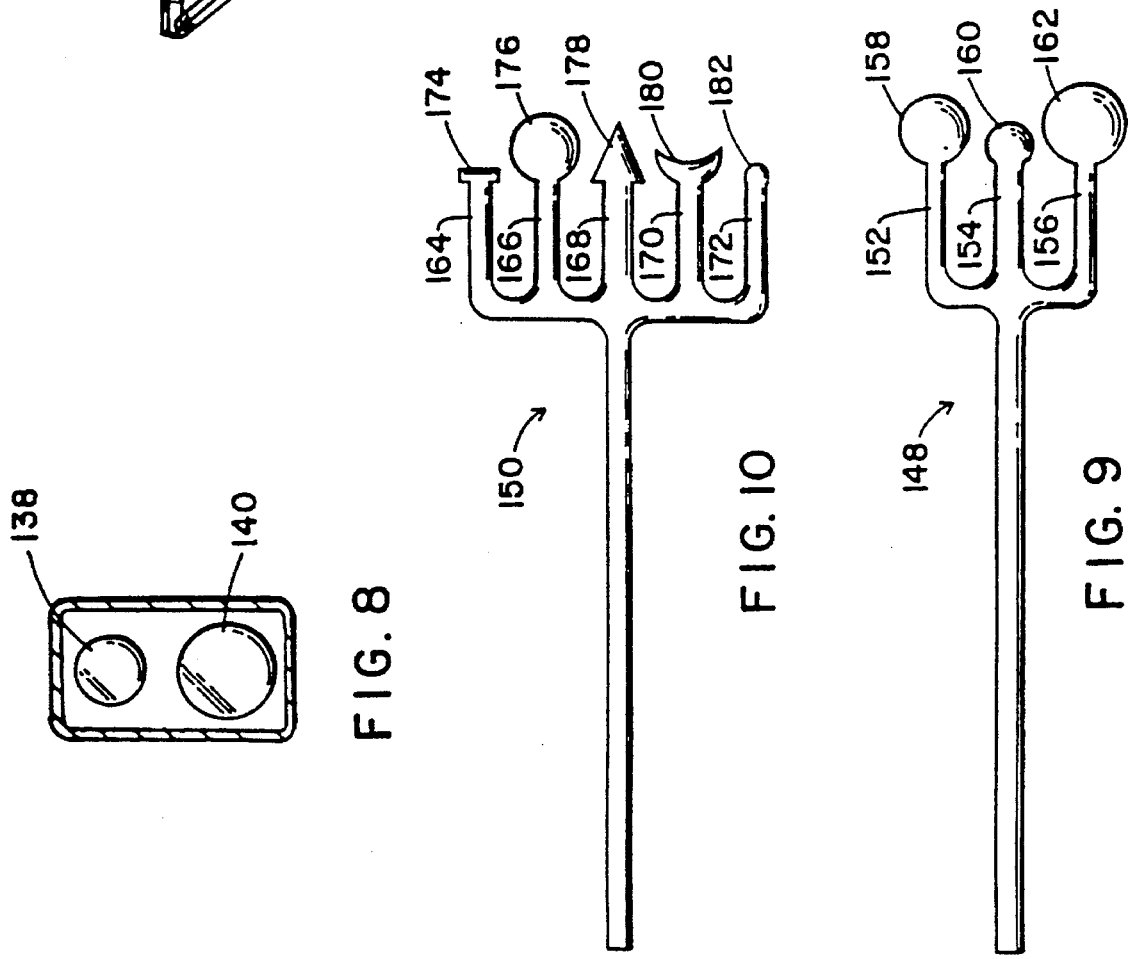

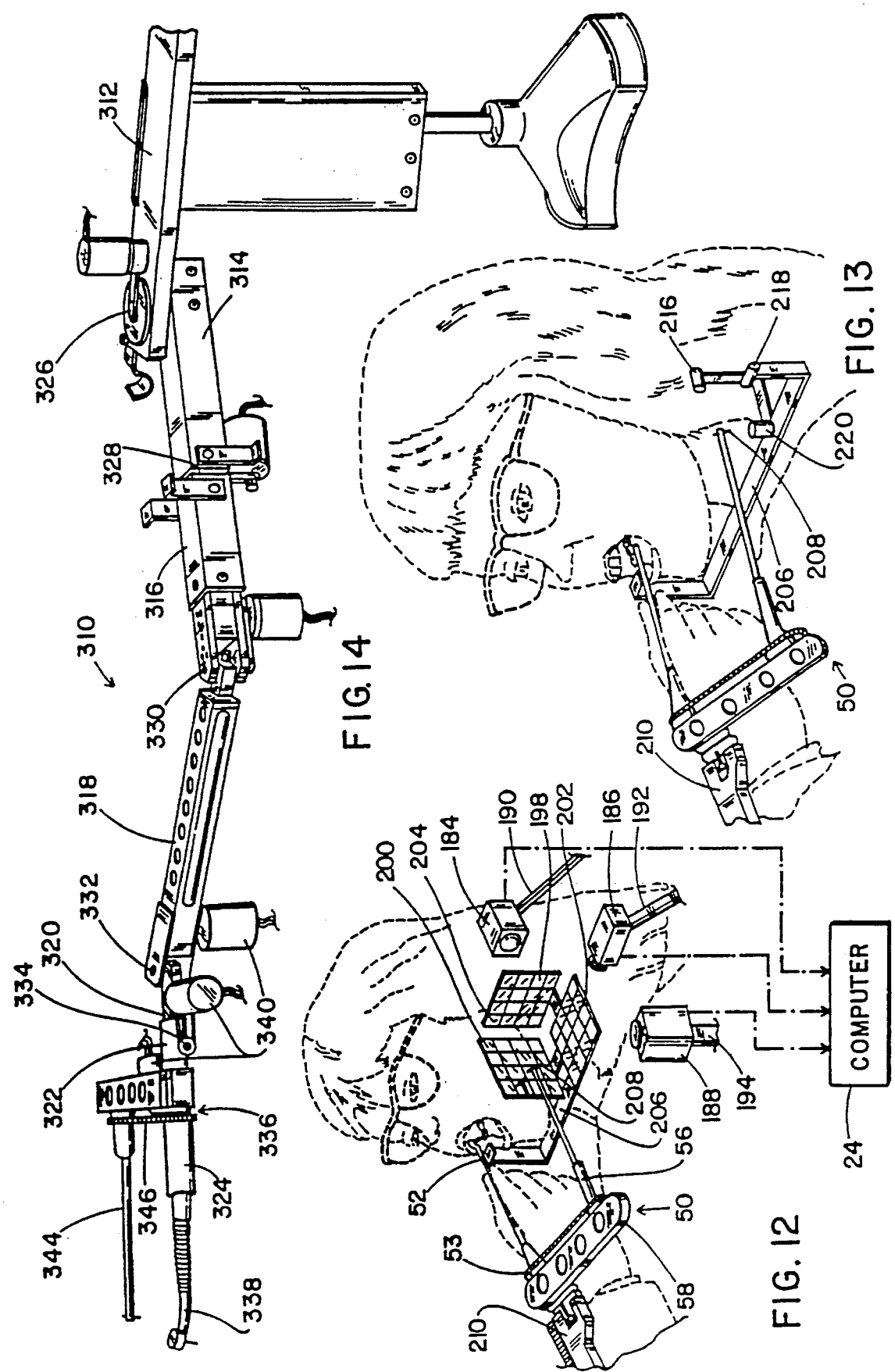

5,562,448

METHOD FOR FACILITATING DENTAL DIAGNOSIS AND TREATMENT

CROSS-REFERENCE TO A RELATED APPLICATION

This application is a continuation-in-part of commonly owned U.S. patent application Ser. No. 507,162 filed Apr. 10, 1990 and commonly owned U.S. patent application Ser. No. 694,446 filed May 1, 1991.

FIELD OF THE INVENTION

This invention is directed to a series of related methods for facilitating dental diagnosis and treatment. More particularly, this invention relates to a method for use in forming a preparation in a patient's jaw. This method is useful, for example, in anchoring a dental implant in a jaw of a patient. A related method entails conducting a practice operation on the patient. In addition, this invention relates to a method for instructing and possibly monitoring an actual operation on the patient.

This invention also relates to a method for providing information as to a patient's dental condition, and more particularly, a method for producing an electronic chart of a patient's dentition. This invention further relates to a method for at least partially automatically making a dental diagnosis.

Another method in accordance with the invention provides a computer with data regarding a dentitious structure, e.g., within a tooth, surrounding the tooth or within a bone, of a patient. Yet another method in accordance with the present invention serves in the formation of a dentitious preparation.

BACKGROUND OF THE INVENTION

U.S. patent application Ser. No. 507,162 discloses a system for modifying the shape of a three dimensional object such as a tooth in a patient's mouth. The system includes a pantograph type assembly for feeding to a computer digitized data representing surface contours of the tooth. The pantograph assembly includes a hand-held probe inserted into the patient's mouth by a dentist. The dentist manipulates the probe so that a stylus tip of the instrument is held in contact with the tooth during tracing of a contour along the tooth. A pantograph extension outside the patient's mouth tracks the motion of the probe and particularly the stylus tip thereof, the motion of the pantograph extension being monitored by cameras which transmit video signals to the computer.

The computer shows on a monitor a graphic representation or image of the tooth. This image is generated from the digitized contour data and possibly also video data from an optical probe. In addition, the computer is preprogrammed with data on prosthetic dental appliances and/or dental restorations, forms of which are provided in a kit. These forms may be in a variety of materials. Images of these prosthetic appliances and/or restorations may also be displayed on the monitor under the control of the computer.

Such a system, including its software, presents an opportunity to advance in additional ways the daily practice of dentistry. For example, pocket depth information is conventionally obtained by visually reading a ruler on a stylus which is inserted into gingival pockets. The depth information is stored as numbers on a form or a sketch outlines on the form. More recently, the pocket depth information is available in the form of a chart print out upon manual transference of the depth information to a computer. Each such chart is a printed form with outlines of squares, circles and rectangles representing the individual teeth positions in a dental arch. Horizontal lines crossing the tooth symbol outline serve as measured demarcations in reference to root shapes. Roots are thus represented as two-dimensional shapes, outlined below the two-dimensional rectangular or ovoid shapes of the crowns.

The horizontal lines serve as printed references. Each line is an increment for measurements. In this way, pocket depth information is mapped in chart form. Various inaccuracies inherent in the current measurment methodology are carried into the examination data and are entered into the chart record as a subjective notation.

An X-ray film of a tooth or other dentitious structure contains a great quantity of useful information. However, X-ray data is obtained separately from the periodontal clinical data and both classes of data are read separately.

Further dental information obtained from direct observation include determinations of mobility, gingival thickness, presence of bleeding, calculus, etc. These observations are separately and manually noted on a chart.

Accordingly, current dental diagnostic practice involves a variety of different observational techniques; the results of the different observations are generally obtained or recorded in different media and thus in different places. Currently, there is no integrated diagnostic information store or single method of storing and presenting all the different observational results.

Another way of storing and presenting dental data is the study model. Study models are conventionally made of stone or plaster, although more recent technologies are based on more modern materials such as synthetic polymeric materials. Study moderls are necessary, or at least useful, in the diagnosis and treatment of bone disease, gum conditions and missing teeth.

Dental implants constitute a relatively recent development in dental practice and/or treatments. In an implant, the jaw bone of a patient is drilled to form a bore which receives a blade or anchor for an implant crown. To produce a desired and proper osseo integration and prosthetic and/or restorative placement of supra gingival restoration on the implant in its functional occlusal position, the dental practitioner or surgeon must precisely control the position, orientation and insertion of the blade or anchor. The ultimate position and orientation of the blade must take into account the thickness of the bone at the area of the implant, the proximity and orientation of adjacent teeth in the same jaw, and the location of teeth in the opposing jaw. In proper conventional implantation surgery, two or three people view the drill from different angles, to determine that the drilling is at a proper angle and location. Even under these circumstances, it is difficult to control the drilling operation so that the position obtained and orientation of the implant blade is optimal or acceptable.

OBJECTS OF THE INVENTION

A general object of the present invention is to provide a method for facilitating the shaping or shape modification of an object, particularly a tooth or other dental structure.

A more specific object of the present invention is to provide such a method which is computer analyzed, guided or controlled.

An additional object of the present invention is to provide a method for enabling a dental practitioner to practice a technique without actually modifying or operating on a patient's dentition or bone structure.

Another, more particular, object of the present invention is to provide a method for providing instantaneous feedback to a dental practitioner or student as to motions of a dental instrument held as it is used or guided by the practitioner or student.

Yet another particular object of the present invention is to provide a method for automatically showing a dental practitioner or student a preferred tool position and orientation in making a dental preparation.

A further object of the present invention is to provide a method for storing together and presenting together different dental observations and measurements, particularly, observations and measurements made in different ways. Thus, an object of the present invention is to provide a method for facilitating the storage and presentation of dental diagnostic information. More specifically, it is an object of the present invention to provide an electronic study model incorporating various classes of input, such as X-ray data and/or pocket information. An associated object of the present invention is to provide a method for facilitating the production of a study model (an electronic study model).

An additional object of the present invention is to provide an improved method for preparing a dental bone of a patient for receiving an implant. A related object of the present invention is to provide an improved method for positioning and orientation an implant blade.

Yet another object of the present invention is to provide an improved method for monitoring the formation, in a patient's jaw bone, of a bore for a dental implant.

An associated object of the present invention is to provide a method for at least partially automatically monitoring the drilling in an implant operation.

SUMMARY OF THE INVENTION

A method for use in forming a preparation in a patient's jaw comprises, in accordance with the present invention, the steps of (a) generating electrically encoded data specifying pre-existing dental structure for edentulous patients or those with at least one tooth, (b) transmitting the data to a computer, (c) operating the computer to generate, on a monitor connected to the computer, a graphic representation of the pre-existing structure, (d) further operating the computer to predetermine an optimal position and an optimal orientation of a material removal tool with respect to the pre-existing structure, and (e) additionally operating the computer to generate, on the monitor, a graphic representation of the tool in the optimal position and the optimal orientation relative to the pre-existing structure.

Although this method has applications in virtually all areas of dentistry, it is especially useful in boring through hard or soft tissues and preparing a site for anchoring a dental implant in a jaw of a patient. In that situation, the pre-existing structure includes bone in the patient's jaw, while the preparation comprises a bored structured form that has been in the jaw bone for receiving a form or blade for the implant. The optimal position and the optimal orientation of the drilling or material removal tool are adapted to produce a desired position and a desired orientation of the blade or anchor for the implant. In this particular procedure, it is advantageous to generate, on the monitor, a graphic representation of the blade in the desired position and the desired orientation relative to the bone and the tooth.

Pursuant to another feature of the present invention, the step of generating electrically encoded data comprises a first step of generating digitized surface data and a second step of generating digitized X-ray data. Both kinds of data are necessary for using the method to implement a dental implant. The digitized surface data may include, for example, video surface data and/or contour data generated with the aid of a probe. The X-ray data and the surface data are correlated to produce a composite image showing both internal and external structures in the precise geometric relationships they have to each other in the patient's mouth. This composite image may in turn be enlarged or expanded, modified or highlighted and shown in different views or sections, for example, to facilitate comprehension of the patient's dental structures.

In accordance with another step in a method pursuant to the present invention, the computer is instructed to modify the optimal position and the optimal orientation of the dental tool and is operated to generate, on the monitor, a graphic representation of the tool in the modified position and orientation relative to the pre-existing structure.

A method in accordance with the present invention may be used to conduct a practice operation on the patient. In such a practice operation, the dental practitioner orients a dental type instrument (e.g., a probe or a drill) in juxtaposition to the pre-existing structure at the optimal position (shown on the monitor), such optimal position having been determined from information stored and/or recorded from standard practise procedures, or taught methodologies, or computed and/or analyzed parameters based on text practise tutorial systems. The computer is provided with electrical feedback or signals as to the actual position and the actual orientation of the instrument. The computer is then operated to automatically determine an angle between the optimal orientation and the actual orientation. The computer then alerts the dental practitioner as to the deviation, if any, between the instrument and the optimal position (obtained from stored intelligences resources) and orientation thereof.

The instrument used by the practitioner in the practice exercise may take the form of a practice instrument having a virtual tip, that is, a non-operational tip. Such a tip may be a flexible stylus or a telescoping member.

Alternatively or additionally, a method in accordance with the present invention may be used to instruct and possibly monitor an actual operation on the patient. Pursuant to this feature of the present invention, the tool (e.g., drill) is used to modify the pre-existing dental structure to form the desired preparation (shown on the monitor). The computer is supplied with electrical feedback as to motions of the tool and modifies the graphic representation on the monitor in accordance with motions of the tool to show modifications of the pre-existing structure.

Advantageously, the computer provides the dental practitioner operating the dental tool with an alert signal regarding deviation between an actual position and orientation of the tool during the use of the tool on the patient and the optimal position and the optimal orientation, as determined prior to the dental operation. The alert signal may take the form of an auditory signal, for example, a verbal message or instruction synthesized by the computer. Alternatively or additionally, the alert signal may include a visual indication provided on the monitor. An alert signal may also be provided in a practice operation, to indicate to the operator a deviation or a conformity of the practice instrument to the predetermined, recommended position and orientation thereof.

Pursuant to another feature of the present invention, the pre-existing dental structure of the patient is analyzed to determine position and orientation of a desired preparation. Thus, for example, if the dental structure includes teeth on opposite sides of a missing tooth, the teeth may be analyzed to determine their positions and orientations and the desired position, size and orientation of a crown to be attached to an implant blade or anchor at the gap. The analysis may include the determination of different virtual or imaginary structures, such as an occlusal plance or a lingual buccal tilt, axes of symmetry and different parameters of a dental arch.

The analysis may supplemented with the steps of (a) at least partially automatically accessing an electronic inventory of digitized prosthetic dental devices corresponding to respective actual dental devices of an actual inventory, and (b) at least partially automatically comparing the digitized prosthetic dental devices in different positions and orientations to the pre-existing structure to determine an advantageous position and orientation of a recommended dental device with respect to the pre-existing structure. For example, in the event that an implant is to be inserted, the actual dental devices of the inventory include blades, anchors, and angle elements for dental implants.

Pursuant to a further feature of the present invention, the step of operating the computer to generate a graphic representation includes the step of operating the computer to generate, on the monitor, graphic representations of a plurality of views of the pre-existing structure. At least one of the views may be generated by the computer upon interpolation of the electrically encoded data. For example, the thickness or breadth of the root of a tooth (as visible in a distal to mesial view of the tooth) may be obtained by interpolating or calculating on the basis of the root depth and width, as seen in an X-ray of the tooth from the buccal side. The interpolated dimensions are easily determined from available statistical information, such as U. G. Blacks's measurment data.

The electrically encoded data advantageously includes X-ray data and contour or surface data as to the pre-existing structure.

A method for providing information as to a patient's dental condition, and more particularly, a method for producing an electronic chart of a patient's teeth, comprises, in accordance with the present invention, the steps of generating first electrically encoded data as to external tooth surfaces in the patient's mouth and transmitting the data to a computer, generating second electrically encoded data as to internal structures in the patient's mouth and transmitting the second electrically encoded data to the computer, and providing the computer with electrically encoded coordinate reference data to enable the computer to correlate the first electrically encoded data and the second electrically encoded data. The computer then generates, on a monitor connected to the computer, a composite graphic representation of at least some of the external tooth surfaces together with at least some of the internal structures.

An electronic chart which results from practicing the above-described method stores together and presents together different dental observations and measurements, particularly, observations and measurements made in different ways. More particularly, the electronic chart combines X-ray data and surface data into one storage medium and enables the presentation of both kinds of data simultaneously. An electronic study chart implemented in accordance with the present invention presents internal structural features and external structural features together, showing the geometric and dimensional relationships among the various structures. Clearly, the presentation and use of the dental information greatly facilitates the daily practice of dentistry.

It is to be noted, moreover, that an electronic study model in accordance with the present invention can incorporate various classes of input. More specifically, the electronic study model can include the surface anatomies of dental structures, X-ray data pertaining to the same structures, periodontal information such as pocket depths and pocket outlines, arch relationships and other bite information such as occlusal contact points and stress analyses.

Pocket information is obtained by contour tracing done with a probe in accordance with the invention of U.S. patent application Ser. No. 507,162. Such a probe is capable of collecting contour data beneath the gums. In accordance with the present invention, the gingival contour data is integrated with X-ray data to provide a complete map of the pocket lines and depths which is represented in graphic relation to bone contours.

The electrically encoded coordinate reference data for enabling the coordination of the X-ray data and surface data may be produced in part by attaching an X-ray opaque reference element to a dental surface in the patient's mouth. The position of the X-ray opaque reference element is then automatically recorded as part of the X-ray data and is additionally incorporated into the surface or contour data, whereby the two kinds of data (external and internal) may be correlated to produce an integral composite image.

Preferably, the X-ray opaque reference element is attached to the occlusal surface via an X-ray transparent connector. Alternatively, where there are no teeth the X-ray opaque reference element takes a saddle-like form and is laid on an edentulous gum surface in the patient's mouth.

Pursuant to an additional feature of the present invention, the computer is operated to distinguish different dentitious structures of the patient and to display the different structures in respective colors or in visually distinguishable textural patterns on the monitor. Such different structures may include different substructures of a tooth. The computer uses various techniques of pattern recognition to determine the different substructures. The patterns include X-ray image density information, texture, shape or contour, and relative location.

This method is particularly valuable in conjunction with the method of providing an electronic study model or chart. The chart thus shows various internal and external dentitious structures in different colors or textural patterns.

In accordance with yet another feature of the present invention, the computer is operated to determine points of contact between teeth of an upper jaw and teeth of a lower jaw and to further determine stress areas in a bone of one of the upper jaw and the lower jaw. The computer may be provided with electrically encoded data as to forces exerted by the teeth of the upper jaw and the teeth of the lower jaw during a biting action. In that event, the computer automatically calculates magnitudes of stress in the stress areas and can be programed to provide diagnostic analysis.

As mentioned hereinabove, a selected dimension of an internal dental structure may be automatically calculated from a plurality of related known dimensions. For example, the thickness of a tooth root (in a direction from lingual to buccal), is calculated from a width and a depth of the root and the total contours and dimensions of the crown.

According to a further feature of the present invention, pocket depths are at least partially automatically determined through hand held probe trace-outs, the pocket depths being displayed on the monitor.

A method for making a dental diagnosis comprises, in accordance with the present invention, the steps of (i) generating first electrically encoded data as to external tooth surfaces in a patient's mouth and transmitting the data to a computer, (ii) generating second electrically encoded data as to internal structures in the patient's mouth and transmitting the second electrically encoded data to the computer, and (iii) operating the computer to generate, on a monitor connected to the computer, a composite graphic representation of the external tooth surfaces together with the internal structures. The computer is operated to select and match stored information with input data so as to identify an anatomical condition of the patient's dentition based on first electrically encoded data and the second electrically encoded data and to provide an indication of the determined anatomical condition.

Preferably, the anatomical condition is displayed on the monitor in a predetermined color different from a color in which the composite graphic representation is displayed.

Another method in accordance with the present invention provides a computer with data regarding a dentitious structure of a patient. This method comprises the steps of (a) piercing gum tissue in the mouth of the patient with a point of an instrument, (b) moving the instrument in the correctly angled direction so that the point contacts a bone surface underlying the gum tissue, (c) generating a signal indicative of the position of the instrument point in contact with the bone surface, and (d) feeding the signal to the computer. This method is particularly advantageous in the accumulation of data for forming a complete electronic charting or study model of a patient's dentition and analyzing and/or computing space dimensions of bone and/or tooth structures. Also, this method is useful, if not necessary, in providing the practitioner with significant data to optimize the orientation and placement of a dental implant. It is advisable in such operations to be aware of the bone contours or surfaces.

Yet another method in accordance with the present invention serves in the formation of a dentitious preparation and comprises the steps of displaying on a monitor a graphic representation in a first color of three-dimensional dental structure in a patient's mouth and also displaying on the monitor, in a second color different from the first color, a graphic representation of desired preparation of the dental structure, in combination with the graphic representation of the dental structure. A practitioner uses a material removal instrument (e.g., a drill) to remove material from a surface of the dental structure. A graphic representation of an actual modification of the dental structure achieved during that material removal step is then displayed on the monitor, in combination with the graphic representation of the structure. The actual modification is shown in a third color different from the first color.

Pursuant to the invention, then, different stages of an actual preparation are displayable on a computer monitor in different colors of a predetermined sequence of colors. Thus, it is easy to determine at a glance the status of a preparation in progess. The different colors or hues of the palette may, for example, represent sequential halves of the drill diameter distance.

According to this particular feature of the present invention, a distance is calculated between a first surface defined by the desired preparation and a second surface defined by the actual modification. The third color, i.e., the color of the modified surface, is then selected from an electronic color palette wherein different distances are coded by respective colors, the third color corresponding to the calculated distance. Preferably, the third color is a predetermined color to indicate a spatial difference between the actual modification and the desired preparation.

A method for charting a patient's dentition comprises, in accordance with the present invention, the steps of (i) digitizing surfaces of at least one tooth in the patient's jaw, placing a point of a dental instrument in contact with one of the surfaces, (ii) generating a first electrical signal encoding the location of the instrument point in contact with the one of the surfaces, and (iii) verbally identifying a characteristic of the tooth at the contact location. The verbal identification is converted into a second electrical signal and, partially in response to the first electrical signal and the second electrical signal, a chart of the teeth is produced including an indication of the characteristic at the contact point location.

The identified and displayed characteristic may take the form of a diagnostic condition of the tooth at the contact location. More particularly, the characteristic may be decay or a filling.

A method for preparing a tooth in a patient's jaw comprises, in accordance with the present invention, the steps of (a) generating electrically encoded data as to surfaces of the tooth, (b) transmitting the data to a computer, and (c) operating the computer to generate, on a monitor connected to the computer, a graphic representation of at least one view of the tooth. Also, an electrically encoded preparation preform is selected from resourced dental information that has been programmed and/or organized into a memory of the computer. Upon the selection, the computer is operated to display the electrically encoded preparation preform in overlay as an image on the graphic representation of the one of the views. Subsequently, a dental instrument is used to modify the tooth to assume the shape of the electrically encoded preparation preform, the computer being automatically provided with electrical feedback as to motions of the instrument. The graphic representation is modified in accordance with motions of the instrument to show modifications of the tooth.

Pursuant to another feature of the present invention, the step of operating the computer to generate a graphic representation includes the step of operating the computer to generate, on the monitor, graphic representations of a plurality of views of the tooth. At least one of the views is generated by the computer upon interpolation of electrically encoded surface data. For example, the thickness or breadth of the root of a tooth (as visible in a distal or mesial view of the tooth) may be obtained by interpolating or calculating on the basis of the root depth and width, as seen in an X-ray of the tooth from the buccal side. The interpolated dimensions are easily determined from available statistical information.

A method for use in forming a preparation in a patient's jaw or tooth comprises, in accordance with the invention, the steps of fixing a block of material relative to the patient's jaw so that the block is disposed outside the patient's mouth, providing a practice dental type instrument with a virtual operating tip and also providing a material removal tool enslaved to the practice instrument so that the tool and the instrument move in tandem with one another. The practice instrument is then moved in a virtual or pretend operation as if to form the preparation in the patient's jaw. During the virtual operation, the tool is automatically operated via the enslavement thereof to the practice instrument, so that a recess is formed in the block. An actual dental type instrument with an operative material removal tip is then used to form the preparation in the patient's jaw. The actual dental instrument is coupled to a slave probe which is inserted into and moved in the previously formed recess to thereby guide and limit motion of the actual dental type instrument.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is a perspective view of another contour data generating device usable in a dentistry system.

DETAILED DESCRIPTION OF THE INVENTION

Figure 1:
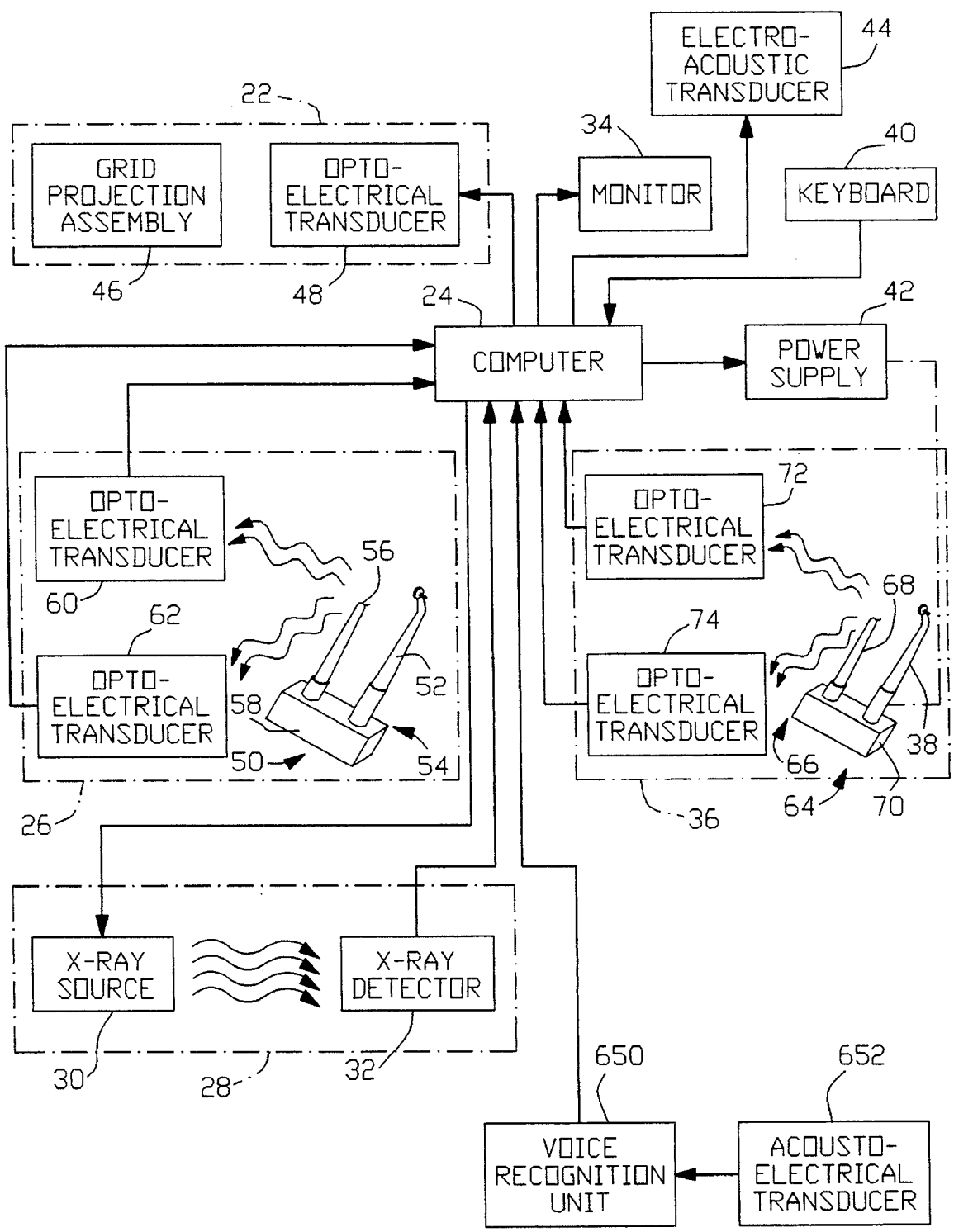
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current extra-oral or intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or stereo or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized information that can be displayed on video as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth and to display such changes through its monitor or video connection.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic resotration). Computer 24 monitors the location of the operating tip of the drill via data generating device 36 and, if the drill approaches a boundary previously defined to the computer from prior programed parameters entered, for example, during an interactive tooth preparation selection operation, then signals are generated that display color changes of material removal information or interrupt the power provided to the drill via a supply 42 or alert the dentist via an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, it is to be appreciated that a grid may be imposed onto the tooth surface by other methods, such as adhesively attaching to the tooth surface a transparency provided with a grid.

As further depicted in FIG. 1 and described in detail hereinafter, data generating device 26 comprises a pantograph-type component 50 which incorporates a stylus handle or holding member 52 and a pantograph extension 54 in turn including a pantograph arm 56 and a bridge element 58. Bridge element 58 connects pantograph arm 56 to stylus holding member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" and forms a graphic model of the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26. The selection of the desired surface area may include outlined boundaries made directly on the patient's tooth with the probe unit. These outline boundaries may be combined with additional programed inputs that include a keyboard and/or a "mouse."

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

Data generating device 36 may be the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
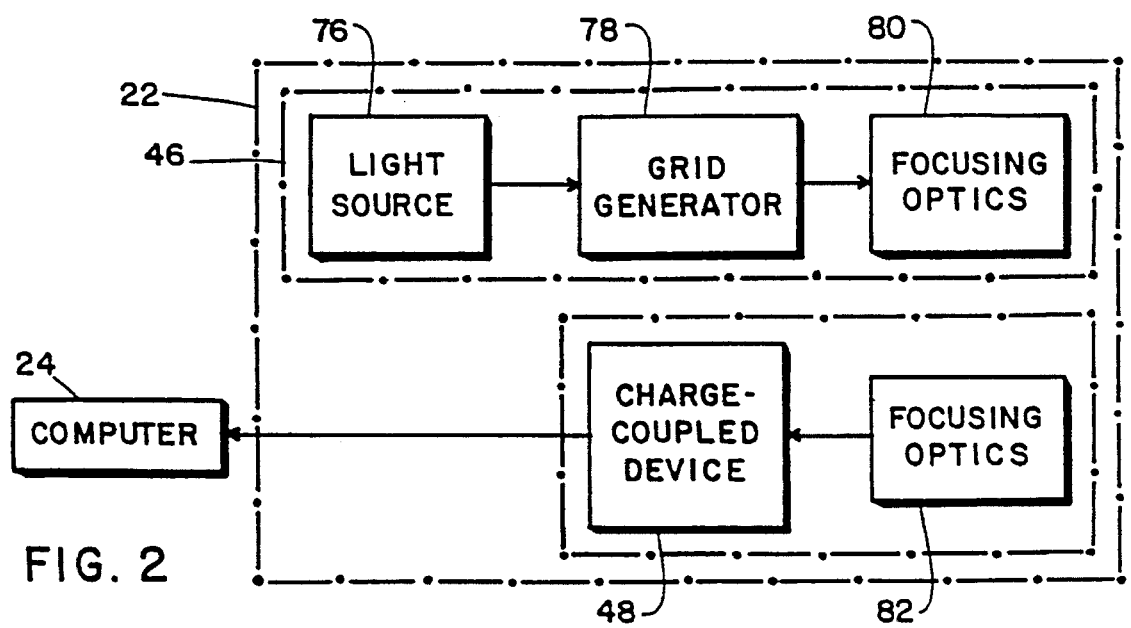
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
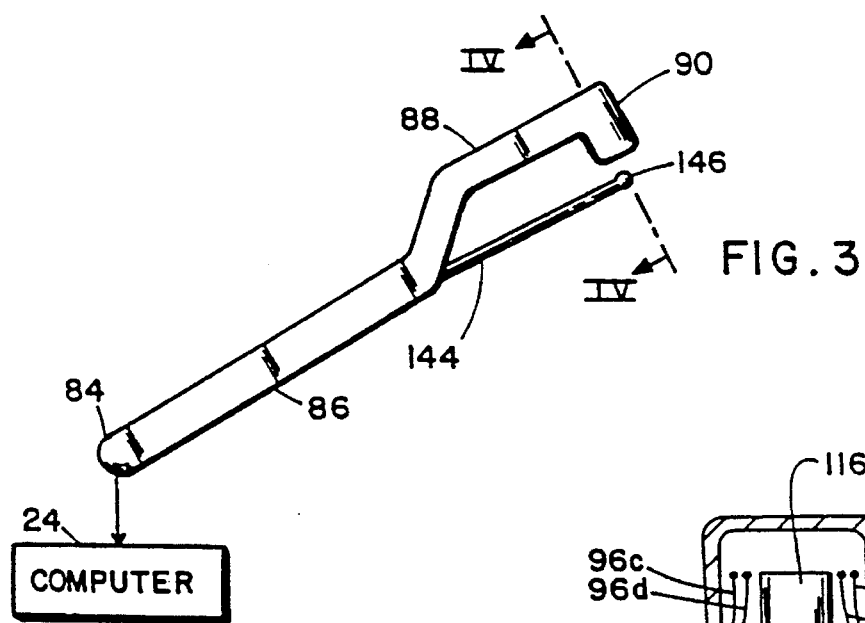
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
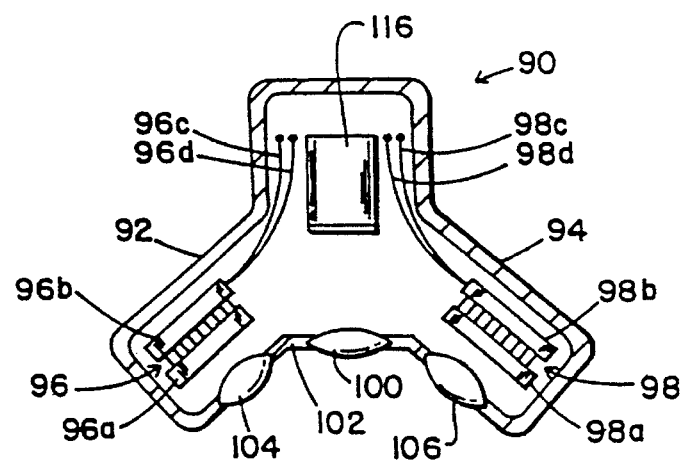
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitve sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
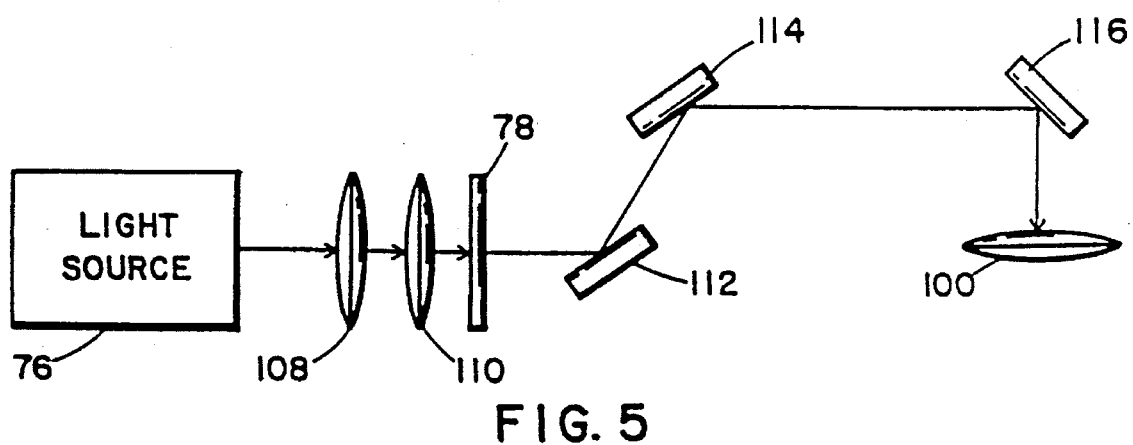
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
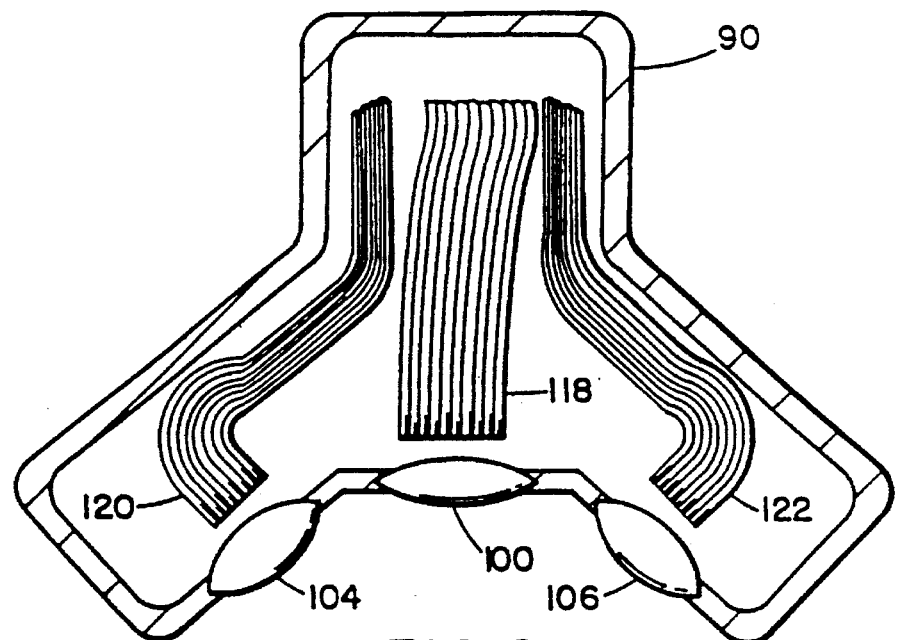
FIG. 6 is a cross-sectional view, similar to FIG. 4, of another particular embodiment of the surface data generating device of FIG. 2.

Grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
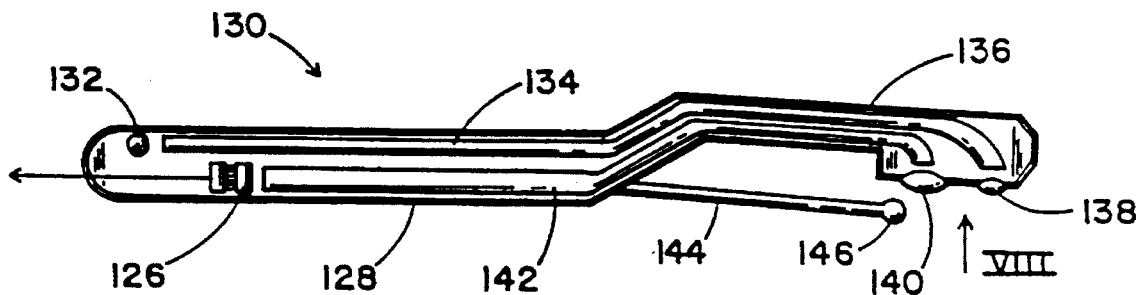
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels correpsonding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIGS. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314–324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326–336 is formed to have sufficient friction to allow the joint to hold a position once placed therein. However, the friction of each joint is low enough so that movement of the joint can be commenced fairly easily.

A plurality of digital encoders 340 are mounted to arm segments 314–324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 maybe provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputing dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In another structural procedure, a dentist and/or operator may use virtual preparation instruments to input specific percentages of tooth removal and to input specific boundaries and depths of tooth removal. The virtual preparation instruments include a telescopic stylus and/or drill substitutes. In yet another alternative procedure, computer 24 may be programed to recognize structural features of the tooth, such as its type, the location and shapes of cavities and prior inlays or onlays and to automatically select a possible preparation in accordance with the recognized features. The computer may be further programed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
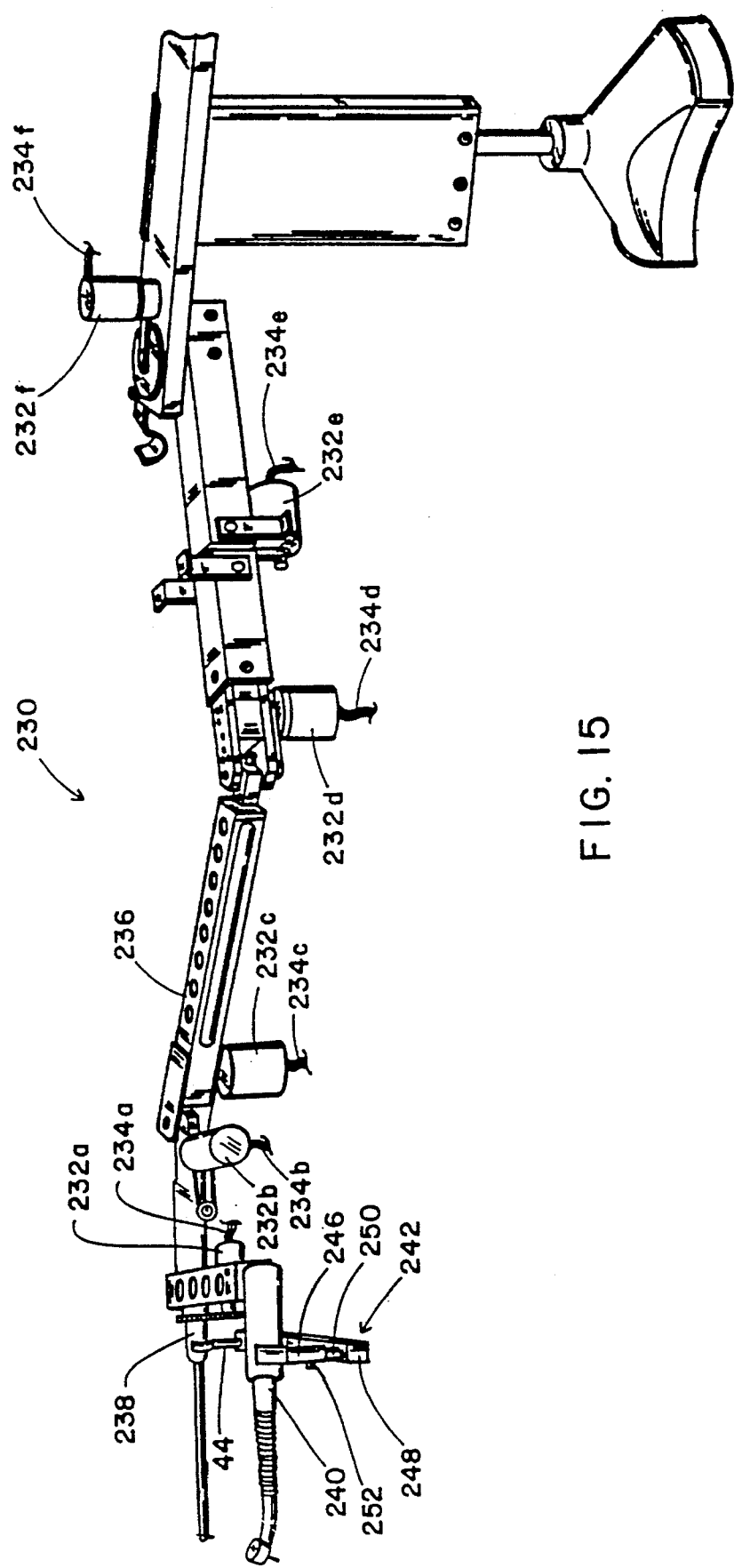
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Limiting the motion of a dentist's drill 254 may be accomplished by selecting a tooth preparation preform 256 from a kit of preparation preforms. Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Figure 16:
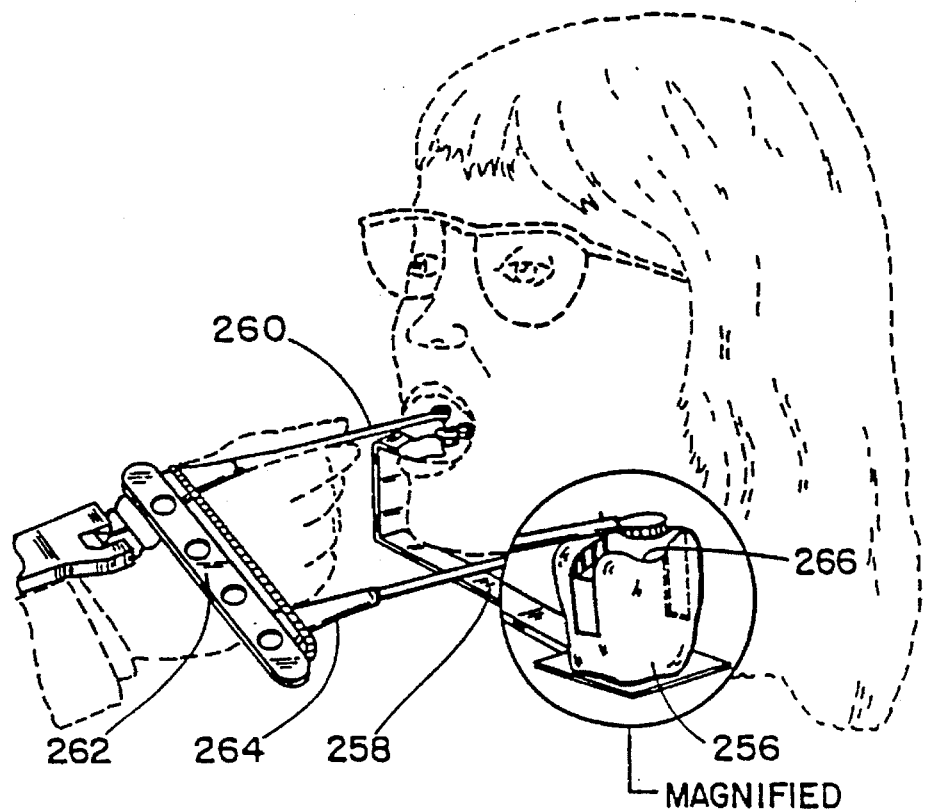
FIG. 16 is a partial perspective view, on an enlarged scale, of a drill movement restriction assembly, showing a tooth preparation preform on an even larger scale.

Accordingly, a kit is provided of dental preparation preforms in different sizes and shapes. Some preforms correspond to shapes of inlays such as that shown in FIG. 16. Other preforms correspond to shapes of onlays or crowns. The kit may also include prefabricated restorations or restorative devices, that is, preformed inlays and onlays for attachment and/or insertion to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic or restorative inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay or crown. If necessary in a particular case, a selected preformed inlay or onlay or crown can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
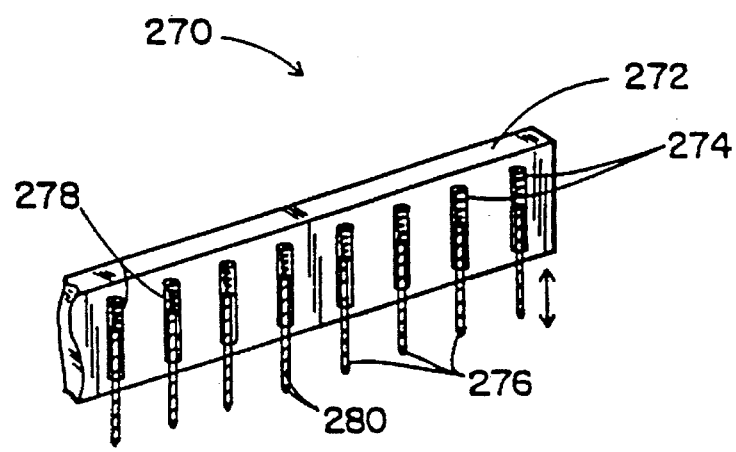
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figure 18:
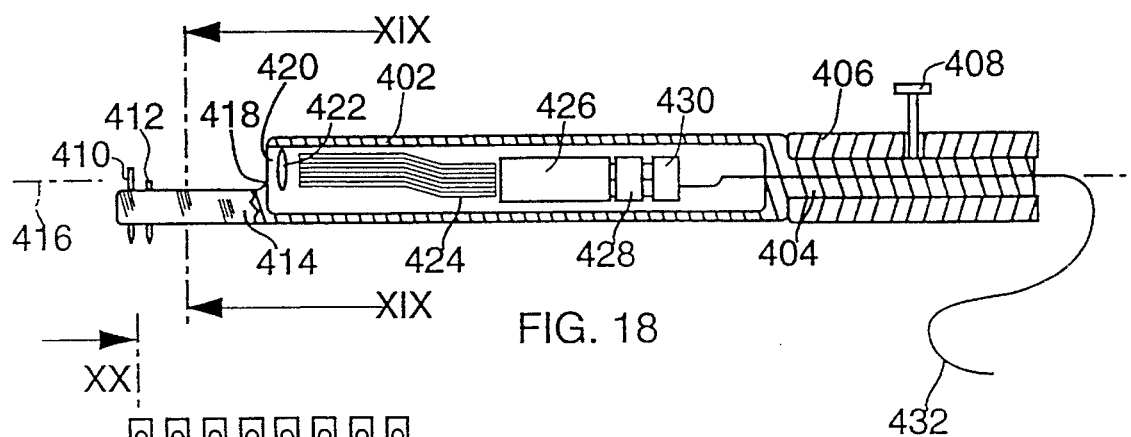
FIG. 18 is a side elevational view, partially in cross-section, of a hand held instrument usable in conjunction with a pantograph assembly illustrated in FIGS. 11–15, for gathering parallel contour data.

As illustrated in FIG. 18, a device for feeding to computer 24 (FIG. 1) contour data as to the surface of an object such as a tooth comprises a hand-held dental instrument or frame 402 provided at a proximal end with an extension 404 removably insertable into a sleeve 406 which forms a part of a pantograph assembly such as that illustrated in FIGS. 11 through 15. Instrument frame 402 is locked in a predetermined position and orientation to pantograph sleeve 406 by a set screw 408.

At a distal end, instrument frame 402 carries two sets of pins 410 and 412 slidably mounted to a nose portion 414 of instrument frame 401 in respective linear arrays extending at an angle, preferably a right angle, with respect to a longitudinal axis 416 of instrument frame 402.

Proximally of nose portion 414, instrument frame 402 has a shoulder 418 in turn formed with an opening or window 420 facing pins 410 and 412. A lens 422 is disposed at window 420 for focusing incoming light on an input end of a bundle of optical fibers 424 extending to a video camera in the form of a charge coupled device ("CCD") 426 inside instrument frame 402. CCD 426 is provided with conventional scanning circuitry 428 and output signal preprocessing circuitry 430. An output lead or multiple 432 extends from preprocessing circuitry 430 to computer 24 (FIG. 1).

Figure 19:
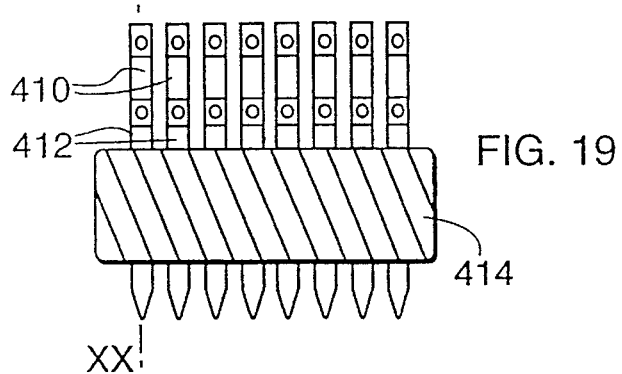
FIG. 19 is a cross-sectional view taken along line XIX—XIX in FIG. 18.
Figure 20:
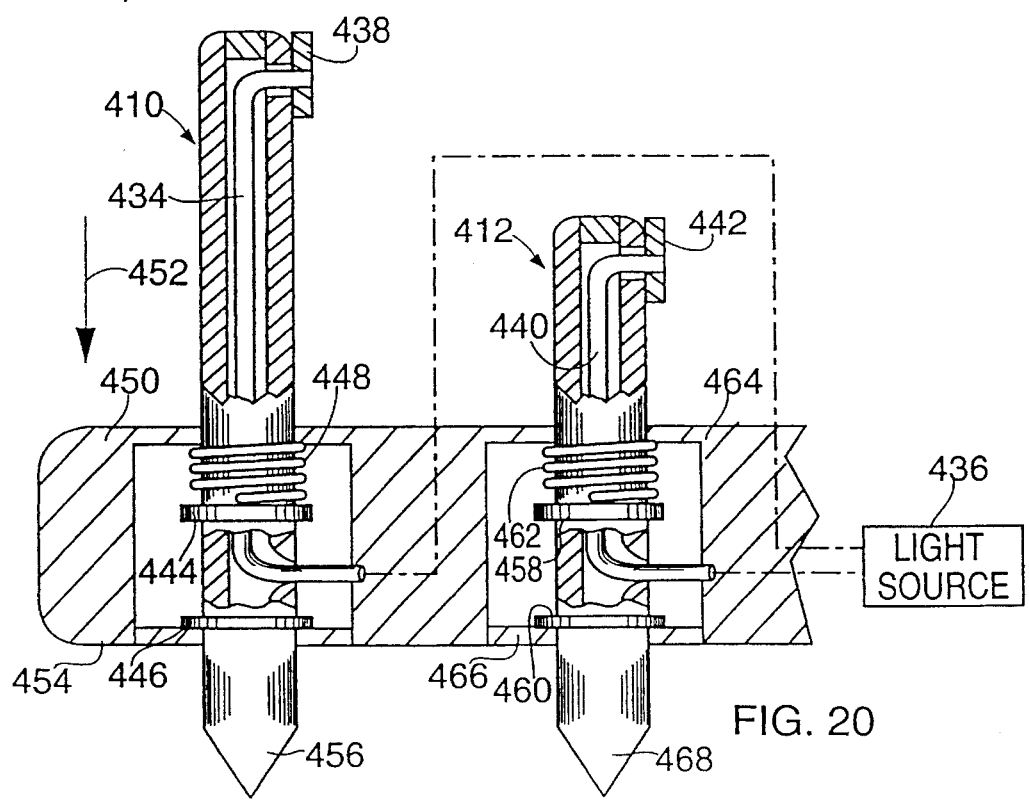
FIG. 20 is a partial cross-sectional view taken along line XX—XX in FIG. 19.

It is to be noted that other configurations of the operative components of the device of FIGS. 18–20 are possible. For example, CCD 426 and its associated circuitry 428 and 430 may be disposed at computer 24 or an intermediate location between the computer and instrument frame 402. In that configuration, optical fiber bundle 424 extends out from instrument frame 402 to the remote CCD. Alternatively, optical fiber bundle 424 may be omitted and CCD 426 positioned in juxtaposition to lens 422.

As depicted in FIGS. 19 and 20, each pin 410 is hollow and contains an end portion of a respective optical fiber 434 extending from a light source 436 inside instrument frame 402 to a mounting bracket 438 at an end of the respective pin 410. Each pin 412 is also hollow and contains an end portion of a respective optical fiber 440 extending from light source 436 to a mounting bracket 442 at an end of the respective pin 412. The distal ends of optical fibers 434 and 440, at mounting brackets 438 and 442, face lens 422, whereby the linear postions of pins 410 and 412 relative to nose portion 414 of instrument frame 402 may be instantaneously and continuously monitored by computer 24 through the video signals received from CCD 426.

As further depicted in FIG. 20, each pin 410 is provided with a pair of spaced perimetrically extending flanges 444 and 446. A helical spring 448 is compressed between a wall 450 of nose portion 414 and flange 444, thereby biasing the respective pin 410 in a direction indicated by an arrow 452. Flange 446 cooperates with another wall 454 of nose portion 414 to limit the distance that a pointed end 456 of the respective pin 410 projects from nose portion 414.

Each pin 412 is provided with a pair of spaced perimetrically extending flanges 458 and 460. A helical spring 462 is compressed between a wall 464 of nose portion 414 and flange 458, thereby biasing the respective pin 412 in a direction indicated by arrow 452. Flange 460 cooperates with another wall 466 of nose portion 414 to limit the distance that a pointed end 468 of the respective pin 412 projects from nose portion 414.

In using the contour data gathering device of FIGS. 18-20, a dental practitioner attaches the instrument frame 402 to pantograph-type component 50 (FIG. 1) via sleeve 406 and set screw 408, thereby fixing the instrument frame and pins 410 and 412 with respect to pantograph arm 56 which is monitored by opto-electrical transducers or video cameras 60 and 62. Pantograph component 50 enables computer 24 to track, from outside the mouth, the translatory motion of an arbitrarily selected reference point on instrument frame 402 inside the mouth of a patient. In addition, described hereinabove, pantograph assembly enables computer 24 to track the orientation of instrument frame 402 inside the patient's mouth. In this manner, computer 24 is continuously informed not only as to the position of the arbitrary reference point, but also the orientation of a coordinate system or reference frame, exemplarily with the reference point as origin.

It is to be noted that other methods for providing computer 24 with data as to the position and orientation of dental instrument 402 are possible. Instead of pantograph assembly, for instance, the encoders and articulated support arm assembly 310 of FIG. 14 may be utilized.

In addition to the data representing the location of an arbitrary reference point on instrument frame 402 inside a patient's mouth and the three-dimensional orientation of the instrument frame, computer 402 is supplied with a data stream from CCD 426 regarding the instantaneous positions of sliding pins 410 and 412. The dental pratitioner presses pointed ends 456 and 468 of pins 410 and 412 against a dental surface and simultaneously draws instrument frame 402 along that surface. During this motion, pins 410 and 412 slide back and forth perpendicularly with respect to nose portion 414 in response to variations (pits and cavities, projections) in the surface of the tooth being scanned. These reciprocating motions tracing a plurality of parallel contours along the tooth surface are sensed by CCD 426 and quantized by computer 24 to form parallel contour data utilizable by conventional CAD/CAM programs previously loaded into computer 24.

The positional tracking of pins 410 and 412 by CCD 426 and computer 24 is facilitated by light output of optical fibers 434 and 440. Computer 24 measures the motions of pins 410 and 412 relative to the arbitrary reference point. Moreover, computer 24 is able to instantaneously correlate the incoming contour data stream(s) with the tooth surface being scanned, owing to the incoming rotational data as to the orientation of instrument frame 402 inside the patient's mouth.

Pins 410 and 412 are shown in FIG. 19 as being aligned with one another along the longitudinal axis 416 of instrument frame 402. However, contour data is collectible at an enhanced rate if the pins 410 of one row are staggered with respect to the pins 412 of the other row. Such a two-dimensional array of pins 410 and 412 enables a greater pin density, thereby increasing the amount of incoming contour data.

Instrument frame 402 may be provided with a button (not shown) which, when pressed by the dentist, provides computer 24 with a signal that contour data input is commencing.

Figure 21:
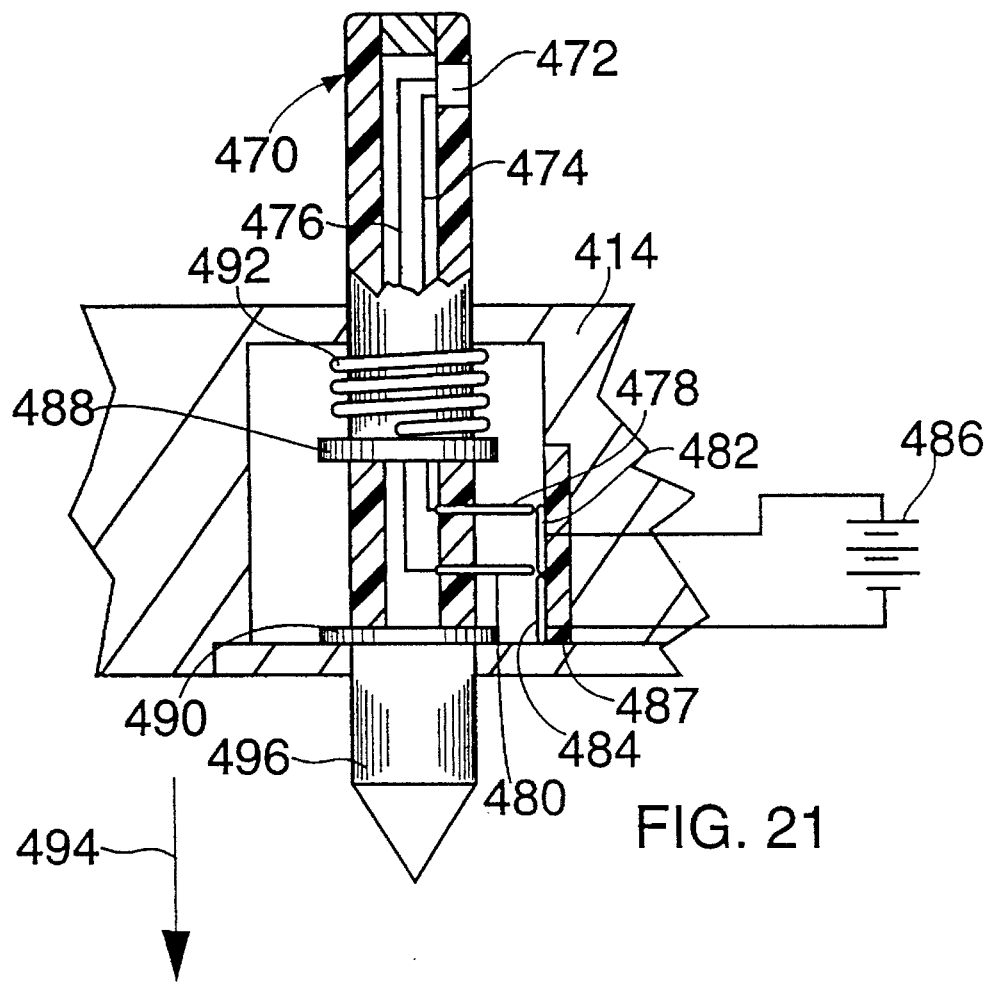
FIG. 21 is a partial cross-sectional view similar to that shown in FIG. 20, showing a modified parallel contour data gathering device.

FIG. 21 depicts another pin or stylus 470 slidably mounted to nose portion 414 of instrument frame 402 in substitution for pins 410 and/or 412. In pin 470, a light-emitting diode 472 forms the light source for facilitating detection by CCD 426 (FIG. 18) and monitoring by computer 24. Diode 472 is connected by a pair of leads 474 and 476 to two brush-type terminals 478 and 480 which are in sliding contact with respective plates 482 and 484. Plates 482 and 484 are connected to opposite terminals of a direct-current voltage source 486 and are insulated from nose portion 414 by a buffer element 487.

As further depicted in FIG. 21, each pin 470 is provided with a pair of spaced perimetrically extending flanges 488 and 490. A helical spring 492 is compressed between wall 450 or 464 (see FIG. 20) of nose portion 414 and flange 488, thereby biasing the respective pin 470 in a direction indicated by an arrow 494. Flange 490 cooperates with wall 454 or 466 of nose portion 414 to limit the distance that a pointed end 496 of the respective pin 470 projects from nose portion 414.

Figure 22:
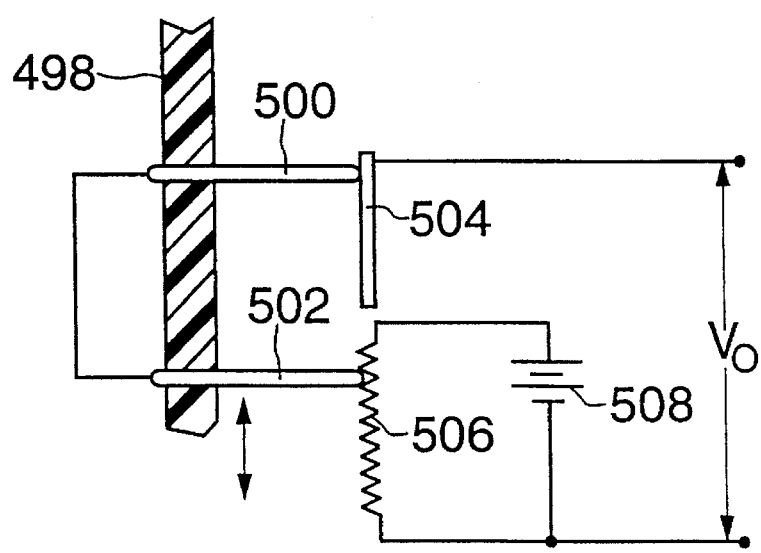
FIG. 22 is a diagram showing a circuit of another parallel contour data gathering device.
Figure 23:
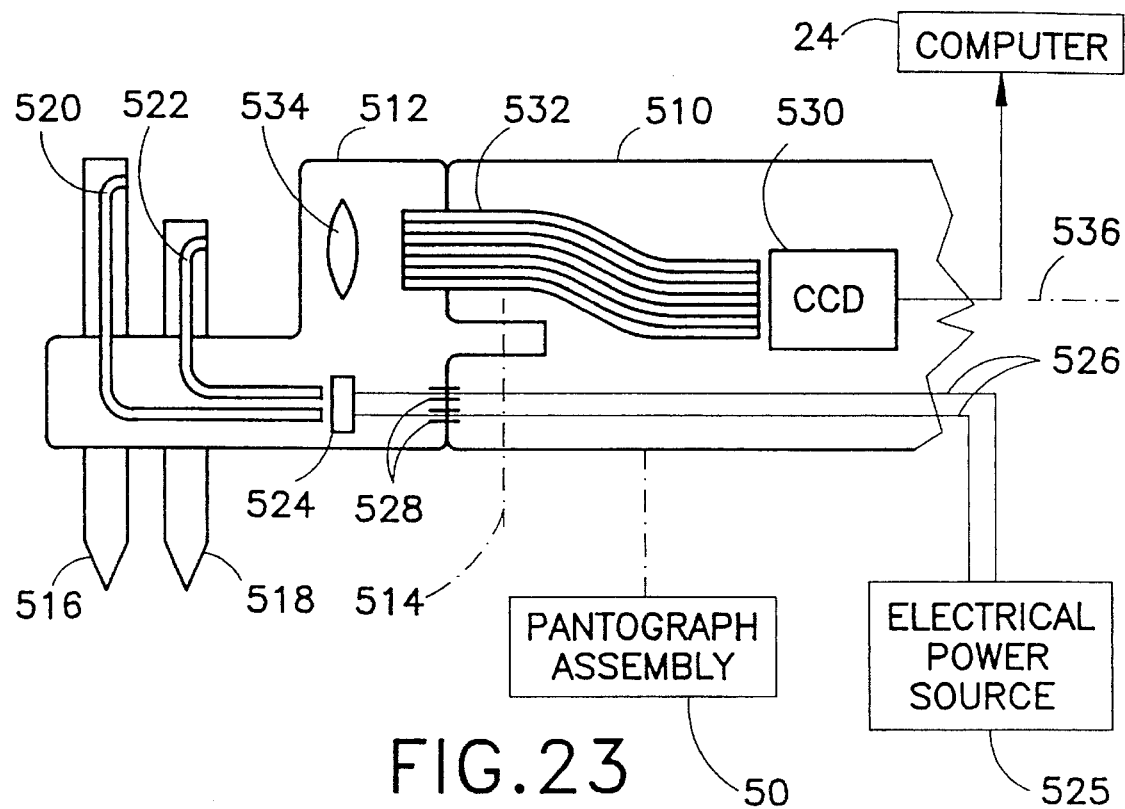
FIG. 23 is a schematic side elevational view of yet another parallel contour data gathering device.

FIG. 22 illustrates a portion of a pin or stylus 498 slidably mounted to a nose portion (e.g. 414 in FIG. 18) of a dental instrument for providing computer 24 (FIG. 1) with digitized data representing a surface contour on a tooth. As described hereinabove with reference to FIGS. 18-20, pin or stylus 498 is one of a plurality of identical stylii all slidably in nose portion 512. Diode 524 in turn is energized by a source of electrical power via a pair of leads 526. Leads 526 include a pair of sliding or brush type contacts 528 for enabling the conduction of electrical energy to diode 524 over the rotating link between frame 510 and nose portion 512.

A reciprocating type motion of pins 516 and 518 which occurs as a dentist moves nose portion 512 along a tooth surface is monitored by computer 24 via digitized video signals arriving from a charge-coupled device ("CCD") and its associated circuitry 530. CCD 530 receives optical energy via a bundle of optical fibers 532 extending from a lens 534 in nose portion 512.

The pivoting attachment of nose portion 512 to frame 510 facilitates the collection of parallel contour data by enabling a dentist to orient nose portion at an angle (e.g. a right angle) with respect to a longitudinal axis 536 of instrument frame 510. The angular orientation of nose portion 512 particularly facilitates the collection of parallel contour data along a plurality of parallel planes oriented at the aforementioned angle with respect to axis 536. Computer 24 is able to take the orientation of nose portion 512 into account by monitoring, via pantograph assembly 50, the direction of motion of the distal end of instrument frame 510 during a data gathering motion thereof.

In addition to being preprogrammed with digitized representations of dental preparation preforms in different sizes and shapes, corresponding to actual preforms in a kit, computer 24 may be preprogrammed with digitized images of intermediate stages in the preparation of teeth to receive the preforms. Thus, each preform in the kit of preforms has in the data memory of the computer 24 a plurality of digitized images, one image representing the preform itself and other images representing intermediate stages or steps in the preparation of the tooth or teeth with which the preform may be used.

Upon the input into computer 24 of digitized data defining the surface of a tooth and upon the selection of a tooth preparation or preform either automatically by computer 24 or in response to instructions received via keyboard 40, computer 24 displays on monitor 34 an image of the tooth, an image of the selected preparation, and an image of an intermediate stage or step in modifying the tooth to attain the selected preparation. These images may me shown sequentially or simultaneously in juxtaposition to one another on the monitor. In addition, the images may be modified, for example, in response to instructions from keyboard 40, to show different perspective views and/or cross-sectional views of the tooth, the selected preparation, and the intermediate stage. Of course, more than one intermediate stage may be shown, if such a multiple display is helpful in graphically explicating the modification of the tooth to achieve the desired structure. It is to be noted that successive intermediate stages may be displayed simultaneously in juxtaposition to each other. Alternatively, the successive stages may be displayed sequentially.

Upon the display on monitor 34 of one or more intermediate stages in the modification of a tooth to achieve the displayed preparation, the dental practitioner operates drill 38 (FIG. 1) to modify the subject tooth initially to attain an intermediate stage and subsequently to reach the final desired preparation.

Of course, as discussed hereinabove with respect to the displayed graphic representation of the tooth, the displayed intermediate stage may be modified by computer 24 in response to instructions from the dental practitioner. Such an on-screen modification would preferably be implemented prior to undertaking a tooth preparation operation.

It is to be noted that the above-described technique for using computer assistance in modifying the shape of a tooth is especially useful to teach students preferred steps in preparing a tooth. Computer 24 is preprogrammed to store in encoded form a plurality of possible final modifications or preparations of a tooth and for each such final preparation at least one respective intermediate stage in modifying the object at its surface to attain the respective modification.

As described hereinabove, the modification of the tooth in accordance with the preprogramed intermediate stage data may be implemented automatically by computer 24 operating under numerical control. Computer 24 thus uses the drill movement control assembly 230 described above with reference to FIG. 15.

It is to be understood that the modification of the tooth may be implemented by a machining or drilling process or more modern techniques such as laser etching.

Pantograph assembly 50 or, alternatively or additionally, encoders and articulated support arm assembly 310 provide a system and procedure for automatically and precisely monitoring the motions of a dental instrument as it is being manipulated, either inside or outside the mouth of a patient. As described hereinafter, the motions and/or positions and orientations of the dental instrument may be recorded for subsequent playback or display on monitor 34. This playback is advantageous, for example, for pedagogical purposes. A skilled dentist or dentistry teacher uses a dental instrument to execute a preferred or ideal technique, and successive positions and orientations of the instrument are input into a computer via pantograph assembly 50 and its attendant cameras or, alternatively or additionally, encoders and articulated support arm assembly 310. Thus, these motion digitization devices are used to digitize the entire motion of a dental instrument or other tool as it approaches and begins work on an object (e.g., tooth) to be modified (e.g., machined or drilled). To receive and store the motion-encoding digital signals, computer 24 need only be programed to recognize when such motion input is occuring. Recognition may be triggered, of course, by appropiate input, for example, via keyboard 40 (FIG. 1).

The initial recordation of a preferred manner of holding the dental instrument (which may be an operating instrument such as a drill or a non-operative instrument such as a periodontic probe) may be implemented using a model or a representative tooth.

Upon the storage of motion data, computer 24 uses the data to illustrate the motion on monitor 34. Such a depiction of instrument motion may take the form of a series of discrete images of different successive positions and orientations of the dental instrument. The successive images may be shown in rapid succession, as in a video presentation, or in slow motion. Alternatively, the successive positions and orientations may be displayed simultaneously in juxtaposition on monitor 34. As yet another alternative, particularly in the event that one position and orientation of the dental instrument is sufficient to demonstrate the preferred instrument use, computer 24 may be operated to show only that one position and orientation of the dental instrument. In addition, to further illustrate the manipulation of the instrument, a graphic representation of a hand holding the instrument is shown on monitor 34. In the event of several successive images, the hand's orientation may change together with the orientation of the instrument.

Upon (a) the feeding to computer 24 of digitized information as to a surface of a tooth, (b) showing on a display a graphic representation the tooth or a portion thereof and possibly a graphic representation of a selected tooth preparation, and (c) the display on monitor 34 of one or more images of a dental instrument in a preferred orientation for accomplishing a desired modification of a tooth to achieve, for example, a selected preparation, the dental practitioner or student manipulates drill 38 (FIG. 1) or a mock drill (e.g., with a telescoping or self-sinkable drill bit) in an attempt to replicate the displayed position and orientation or series of displayed positions and orientations. During this exercise, computer 24 instrument motion may take the form of a series of discrete images of different successive positions and orientations of the dental instrument. The successive images may be shown in rapid succession, as in a video presentation, or in slow motion. Alternatively, the successive positions and orientations may be displayed simultaneously in juxtaposition on monitor 34. As yet another alternative, particularly in the event that one position and orientation of the dental instrument is sufficient to demonstrate the preferred instrument use, computer 24 may be operated to show only that one position and orientation of the dental instrument. In addition, to further illustrate the manipulation of the instrument, a graphic representation of a hand holding the instrument is shown on monitor 34. In the event of several successive images, the hand's orientation may change together with the orientation of the instrument.

Upon (a) the feeding to computer 24 of digitized information as to a surface of a tooth, (b) showing on a display a graphic representation the tooth or a portion thereof and possibly a graphic representation of a selected tooth preparation, and (c) the display on monitor 34 of one or more images of a dental instrument in a preferred orientation for accomplishing a desired modification of a tooth to achieve, for example, a selected preparation, the dental practitioner or student manipulates drill 38 (FIG. 1) or a mock drill (e.g., with a telescoping or self-sinkable drill bit) in an attempt to replicate the displayed position and orientation or series of displayed positions and orientations. During this exercise, computer 24 advantageously monitors the motion via pantograph assembly 50 or, alternatively, encoders and articulated support arm assembly 310. Computer 24 compares the actual motion with the ideal motion, as stored in memory, and displays the results of the comparison on monitor 34. Such results may take the form, for example, of two differently colored images or sets of images. In addition, arrows or other pointers may be used to indicate parts of the actual motion which could be changed in a subsequent exercise to closer approximate the ideal motion. Of course, an auditory alert signal may be generated by computer 24 to indicate deviation from the ideal motion. The alert signal is advantageously sounded during the manipulation of the instrument. As the instrument deviates further and further from the ideal path, the auditory signal may become louder, or change in pitch.

The providing of feedback to a practitioner or student thus includes the step of displaying a graphic representation of at least one actual position and orientation of the instrument attained during the manipulation of the instrument. The graphic representation can be displayed in juxtaposition to the image of the ideal position and orientation of the instrument.

In providing feedback, computer 24 advantageously quantizes differences between the ideal position(s) and orientation(s) and actual positions and orientations taken by the instrument during manipulation of the instrument by the dentist or studnet. The quantized differences are indicated to that person via monitor 34.

Figure 24:
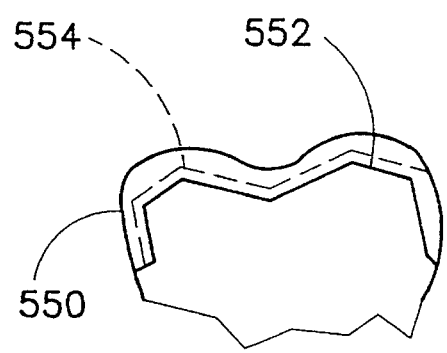
FIG. 24 is a schematic side elevational view of a tooth as it would appear on a computer monitor in accordance with the present invetntion, showing a desired preparation of the tooth and an intermediate stage in the actual preparation.

FIG. 24 represents a graphic representation of a tooth 550 shown on computer monitor 34 (FIG. 1). The external surfaces of tooth 550 are digitized and stored in internal memory of computer 24, as described hereinabove with reference to FIGS. 1–23. In addition, as also described above, computer 24 is operated to select a digitized or electronic preform 552 from an inventory of preparations stored in computer 24. The inventory of electronic preforms advantageously corresponds to a kit of actual preforms which may be inserted into actual preparations upon the formation of the preparations in patient's mouths by a dental practitioner.

Upon selection of preparation 552, either automatically by computer 24 or by the practitioner utiliizing keyboard 40 (FIG. 1), preparation 552 is displayed in overlay on tooth 550 on monitor 34. Preferably, preparation 552 is displayed in a different color from tooth 550.

Although FIG. 24 shows only a single view of tooth 550. It is to be understood that several views may be displayed on monitor 34 simultaneously. For example, tooth 550 may be shown in buccal or lingual elevation, from the mesial direction or in plan view. In addition, one or more cross-sectional views of tooth 550 may be provided. These views may be presented as a matter of course on monitor 34 or, alternatively, the practitioner may instruct computer 24 as to which views are to be displayed. Preferably, the tooth and preparation 552 have the same respective colors in all the various views.

Upon the display of tooth 550 and preparation 552 on monitor 34, the practitioner uses drill 38 (FIG. 1) to modify the patient's tooth 550 pursuant to the desired preparation 552 as displayed on monitor 34. During the modification of the actual tooth, the graphic representation on monitor 34 is altered to conform to the new tooth surfaces, as shown at 554. The new tooth surface 554 is preferably displayed in a color different from the colors of the original surfaces of tooth 550 and the surfaces of preparation 552.

To provide the practitioner with an additional indication of how close the prepared tooth surfaces 554 are to the desired or target preparation 552, the color selected by computer 24 for the new tooth surface 554 corresponds to the distance between the actual tooth surface 554 and the desired preparation surface 552. As the distance between the actual tooth surface 554 and the desired preparation surface 552 changes during the dental operation, the color of new surface 554 on monitor 34 changes. To this end, computer 24 is provided with a preprogramed sequence or palette of selectable colors which may, for example, represent sequential half-drill diameter distances. Thus, it is easy to determine by a glance at monitor 34 the status of a preparation in progess. Of course, computer 24 is programed to continuously calculate distances between the actual tooth surface 554 and the desired preparation surface 552 and to select the color of new surface 554 in accordance with the colors of the palette.

Figure 25:
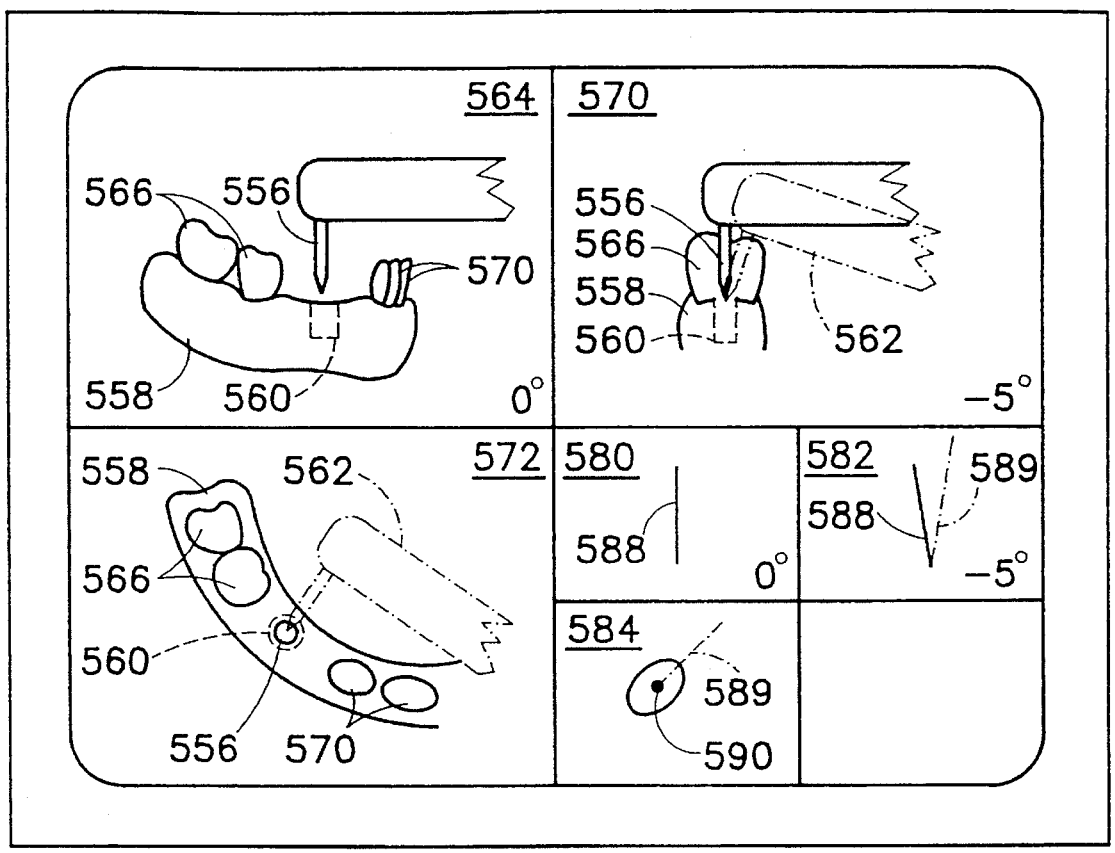
FIG. 25 is a display on a computer monitor, showing optimal and actual orientations of a dental instrument relative to a patient's dentitious surfaces.

FIG. 25 shows a display on monitor 34 of three views of an optimal position and orientation 556 of a drill (not separately enumerated) for cutting into a patient's mandible 558 (or any bone structure) a bore 560 for receiving an anchor or blade (not shown) of an implant. FIG. 25 also illustrates in dot-dash phantom outline an actual position and orientation 562 of the drill during an actual operation, or of a virtual instrument during a practice or trial run.

More specifically, a first screen portion 564 illustrates a buccal or lingual elevational view of a pair of molars 566 and several front teeth 568, as well as a part of jaw bone 558. In a second screen portion 570 is depicted a view of molars 556 from the mesial direction. In a third screen portion 572 is a top plan view of molars 566, front teeth 568 and bone 558. As discussed hereinabove with reference to FIG. 24, other views may include cross-sectional views which are dervied by computer 24 via interpolation techniques.

The external surfaces of teeth 566 and 568 are measured or digitized as described above with reference to FIGS. 1–23. In addition, stylus or probe member 52 (FIG. 1) is used to digitize the surface of jaw bone 558. To that end, stylus member 52 is provided with a sharp stylus 574 (FIG. 1) having a length sufficient long to penetrate gum tissue and contact the bone surface. Upon achieving a contact, the practitioner signals computer 24, e.g., via keyboard 40. The dental practitoner repeats the procedure of piercing the gum tissue in a region about a desired implantation site and taking point data until enough data has been collected for computer 24 to map, via interpolation techniques, the entire surface of bone 558 about the implantation site.

The exact placement of bore 560 may be determined to a greater or lesser extent automatically by computer 24. Computer 24 makes this determination in accordance with (a) surface data as to molars 566 and front teeth 568, (b) surface data as to opposing teeth (bite information, obtained as described hereinafter particularly with reference to FIG. 31), (c) the dimensions and shape of jaw bone 558, and (d) the location of internal bone structures, such as blood vessels such those which occupy inferior alveolar canals, or sinus structures, which are to be scrupulously avoided during the drilling operation. It is to be noted that computer 24, because of the digitized locations of and shape data on the canals and sinuses or other anatomical structures, is in an excellent position to determine the optimal angle and depth of anchor-receiving bore 560.

Data as to internal structures (e.g., blood vessel canals) of jaw bone 558 may be obtained via X-ray data generating device or assembly 28 (FIG. 1). Such internal structures can be displayed on monitor 34. The coordination of the X-ray data as to internal structures and the data collected via optical data generating device or assembly 22 and pantograph data generating device or assembly 26 is implemented as described hereinafter with reference to FIG. 29.

As stated above, computer 24 calculates an optimal position and orientation 556 of a drill for forming bore 560 and displays that optimal position and orientation preferably, although not necessarily, in three orthogonal views such as the buccal or lingual elevational view of screen portion 564, the mesial direction view of screen portion 570, and the top plan view of screen portion 572. To enable a dentist or oral surgeon to practice holding the drilling instrument in the correct position and orientation 556, the drill is attached to the pantograph assembly (e.g., like cutting instrument 38 in FIG. 1). Alternatively, a practice or virtual instrument as those discussed hereinafter with reference to FIGS. 26 and 27 may be attached to the pantograph assembly.

The dentist holds either the actual drilling instrument or a practice instrument in the patient's mouth and manipulates it while watching monitor 34. On monitor 34, the position and orientation 562 of the manipulated instrument is represented in real time in a manner detectably different from the representation of the optimal position and orientation 556 of the drill. For example, the actual position and orientation 562 of the actual or practice instrument may be shown in a different color or in phantom outline, as in FIG. 25.

As shown in FIG. 25, a dentist or oral surgeon is provided with immediate feedback, from at least two different directions, of the position and orientation of an actual or virtual drill relative to the patient's tooth and bone surfaces. This feedback also includes an indication of the actual position and orientation 562 relative to a predetermined optimal position and orientation 556. The indication may include not only an illustration of the relative positions and angles but also numerical angular designations (e.g., 0°, −5°) of the differences between the actual position and orientation 562 relative the predetermined optimal position and orientation 556.

As further illustrated in FIG. 25, the display on monitor 34 may also include one or more screen areas 580, 582 and 584 wherein the representations of the actual position and orientation 562 and the predetermined optimal position and orientation 556 are simplified to lines 588, 589 and points 590.

The feedback as to divergences between actual position and orientation 562 and predetermined optimal position and orientation 556 may alternatively or additionally take an aural form, instructions or information being communicated to the dentist or surgeon via electro-acoustic transducer 44 (FIG. 1). If the instructions or information is in the form of words, those words may be generated with the aid of well known, conventional speech synthesis software and hardware (not illustrated).

Figure 26:
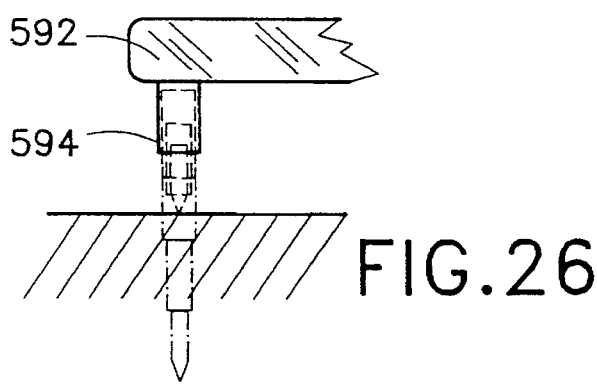
FIG. 26 is a side elevational view, on an exagerrated scale of a dental instrument with a telescoping virtual operating tip for use in a method in accordance with the present invention.

A virtual instrument for use in practice or trial runs is depicted in FIG. 26. The instrument includes a handle 592 attachable to pantograph component 64 (FIG. 1) and a virtual operating tip 594 comprising a telescoping member. Telescoping operating tip 594 enables the dentist or surgeon to practice a drilling operation on the patient without actually penetrating the patient's tooth or tissues (e.g., gingiva, edentulous gum tissue or bone tissue). As discussed above, the dentist or surgeon watches monitor 34 during the practice or trial run, thereby obtaining immediate feedback as to the proper manipulation of the instrument.

Upon satisfactory practice, the dentist or surgeon replaces the practice instrument (FIG. 26) with an implant burr or drill and proceeds with the actual operation. Of course, computer 24 continues to provide both visual and aural feedback to the operator during the actual surgery.

The supplementary techniques described above for computer monitoring of a dental operation are available in an implant operation. Computer 24 may terminate power to the drilling instrument if the angle of penetration deviates more than a preset amount from the predetermined optimal orientation. Alternatively, the drilling operation may be conducted automatically by computer 24 in accordance with the principles of numerical control and with the equipment described above with reference to FIG. 15.

As also described earlier, the dentist or surgeon interacts with computer 24 to determine the optimal position and orientation 556. A selection made by computer 24 may be modified by the practitioner. Moreover, the selection by the computer may be made in accordance with a digitzed inventory of anchors and angle.

It is to be noted that this technique of practice or trial run operations may be performed in areas of surgery other than dental surgery. Generally, the necessary steps include (a) scanning body structures internal to the patient, (b) digitizing the internal structures in response to the scanning, (c) displaying an image of the internal structures in response to the digitized signals, (d) providing a practice surgical instrument with a virtual operating tip, (e) moving the surgical instrument outside of the patient in a simulation of actual surgery on a portion of the internal structure, (f) automatically monitoring the instrument during the step of moving, and (g) displaying a representation of at least the operating tip of the instrument in overlap with the image of the internal structure during the step of moving.

Figure 27:
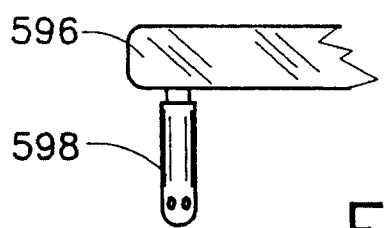
FIG. 27 is a sside elevational view of another dental instrument for use in a practice or virtual operation in accordance with the present invention.

As shown in FIG. 27, practicing an implant procedure may be undertaken with a dental instrument provided with a holder 596 to which an implant anchor 598 is attached. This provides the practitioner with further visual and tactile feedback as to the position and orientation that the anchor will have upon implantation into jaw bone 558 of the patient. The instrumentation shown in FIG. 27 may be modified for placing an implant anchor into a telescoping frame so that actual pressing of the implant into tissue provides a graphic display of the virtual position of the implant as it would be inserted.

Figure 28:
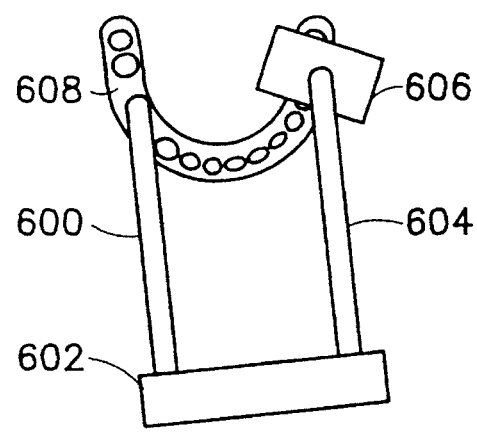
FIG. 28 is a schematic top plan view of an instrument assembly being used in performing a method in accordance with the present invention.

As illustrated in FIG. 28, a practice or trial run of an implant drilling operation may be performed with a practice or virtual instrument 600 mounted to a pantograph assembly 602 which also holds a drill 604. Drill 604 is enslaved to virtual instrument 600, as described hereinabove with respect to FIGS. 1 and 14, so that motions of virtual instrument 600 are duplicated by drill 604. During motions of virtual instrument 600 towards jaw bone 558, as if an actual operation were being performed, drill 604 cuts a bore into a block of acrylic material 606 which has been fastened to the patient's jaw by conventional bonding techniques.

Upon the satisfactory completion of a practice operation, block 606 is provided with a hole (not shown) matching the bore 560 to be formed in the patient's jaw bone 608. The hole in block 606 can then be used as a template to guide, limit or control the motions of an implant drill during an actual operation on the patient's jaw bone 558. Prior to the actual operation, of course, virtual instrument 600 is replaced by an actual implant drill while a drone or probe is substituted for drill 604 in pantograph assembly 602.

As described hereinabove, the system of FIG. 1 includes (a) optical data generating device or assembly 22 for providing a computer 24 with electrically encoded data, specifically, digitized video signals representing a three-dimensional surface of an object such as a tooth, (b) pantograph data generating device or assembly 26 for providing computer 24 with digitized signals containing information pertaining to a curvilinear con tour on the surface of the three-dimensional surface of the tooth, and (c) X-ray data generating device or assembly 28 for providing computer 24 with digitized input signals relating to internal structures of the tooth and surrounding anatomy being scanned.

Figure 29:
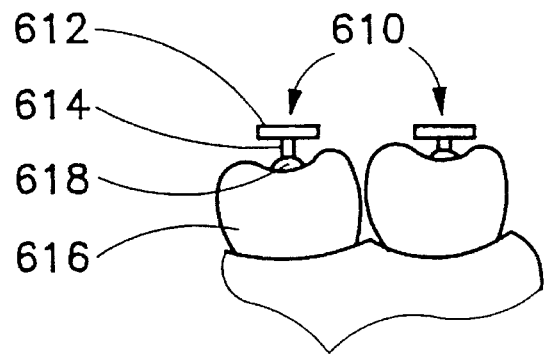
FIG. 29 is a side elevational view of a pair of molars bearing fiducial coordinate frame reference elements in accordance with the present invention.

In order to coordinate the data from optical data generating device or assembly 22 and/or pantograph data generating device or assembly 26, on the one hand, with the data from X-ray data generating device or assembly 28, on the other hand, it is desirable to provide computer 24 with reference data to establish a common coordinate system for both the external surface data from devices or assemblies 22 and/or 26 and the internal structural data from X-ray device 28. As illustrated in FIG. 29, this common coordinate system may be established via the utilization of fiducial reference elements 610 each comprising an X-ray opaque or X-ray detectable portion 612 in the form of a cross-bar of a T shape. The X-ray opaque cross-bar 612 is connected to an X-ray transparent stem 614 in turn cemented to the occlusal surface of a respective tooth 616 at 618. The locations and orientations of reference elements 610 with respect to the external surface data are determined via the use of pantograph data generating device or assembly 26. That device merely traces the shape of cross-bar 612 or a predetermined feature on the surface of the respective reference element 610. The teeth to which the particular coordinate-system reference elements 610 are attached may be entered in computer 24 via keyboard 40. In addition, the identities of the teeth are communicated to computer 24 via X-ray data generating device or assembly 28. Reference elements 610 are provided with distinguishable identifying features detectable via X-ray data generating device or assembly 28. Such identifying features may take the form of a bar code or other markings.

Although FIG. 29 shows T-shaped reference elements, it is to be understood that numerous other shapes may be used.

Figure 30:
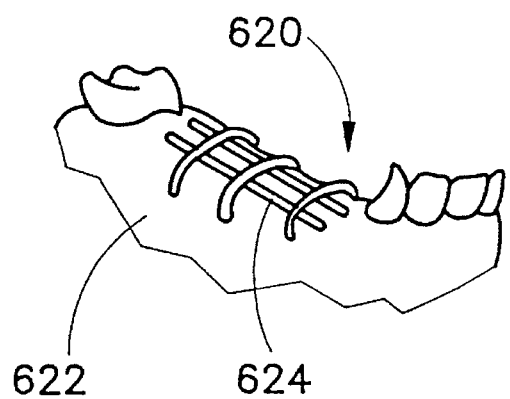
FIG. 30 is a perspective view of another fiducial coordinate frame reference element in accordance with the present invention.

FIG. 30 depicts a coordinate-system reference element 620 in the shape of a saddle mounted on a gum surface 622. Reference element 620 may include one or more X-ray opaque segments or strips 624. The strips may include a bar code or other identification corresponding to the location of gum surface 622.

Data fed to computer 24 via X-ray data generating device or assembly 28 may comprise two or more views of the same tooth from different angles. In that event, computer 24 can use a stereophotogrammetric triangulation program to determine the three-dimensional shapes and dimensions of structures internal to the subject tooth. Alternatively, the thicknesses of internal structures such as roots and nerves may be calculated by computer 24 from the X-ray detectable dimensions and shapes (e.g., widths and lengths) and from statistics correlating the width and length dimensions with thickness dimensions for the different kinds of internal tooth structures. It is to be understood that roots are considered internal structures in this regard because of their dispositions inside the jaw bones.

As yet another alternative, the thicknesses of internal structures may be determined by computer 24 by from X-ray detectable densities. The gray level of a particular feature is therefore indicative of the thickness of that feature.

Computer 24 analyzes external surface data from optical data generating device or assembly 22 and/or pantograph data generating device or assembly 26 and internal structure data from X-ray data generating device or assembly 28 to determine three-dimensional dentitious structures. Computer 24 may be programed additionally to recognize shapes, X-ray densities, textures, and relative locations of different structures in order to identify the different internal tooth structures. Upon identifying the different structures, computer 24 reproduces the structures in graphic form on monitor 34, as illustrated in FIG. 31.

Figure 31:
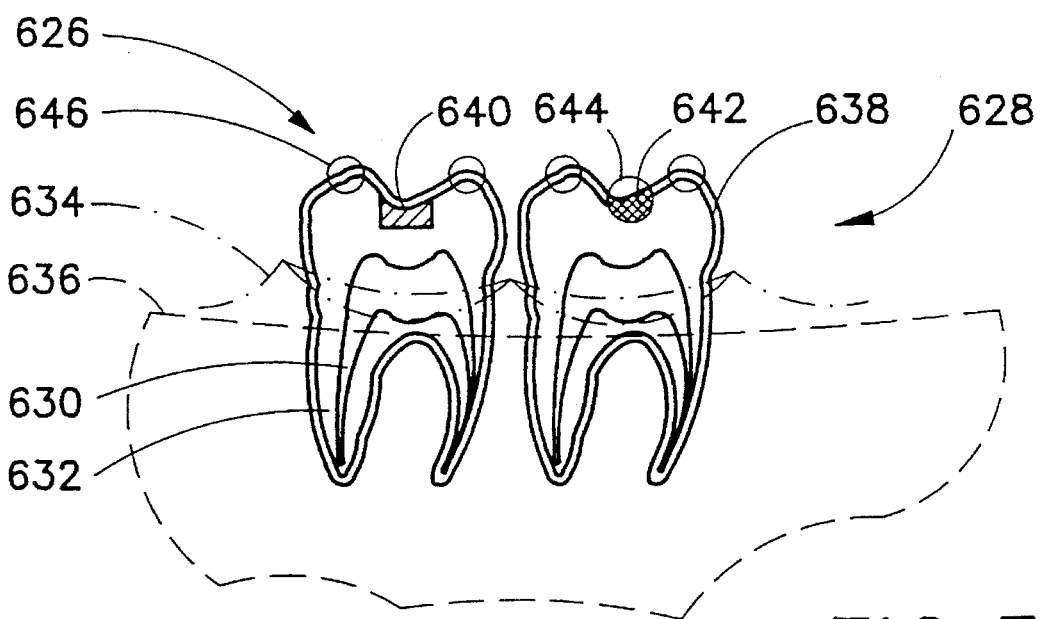
FIG. 31 is a graphic representation, as would appear on a computer monitor in accordance with the present invention, of internal and external structures of a pair of molars.

More particularly, FIG. 31 illustrates an image which computer 24 provides on monitor 34. The image in FIG. 31 is a lingual or buccal elevational view of a pair of molars 626 and 628. Preferably, the different structures of molars 626 and 628, such as the root 630, the pulp 632, the gum 634, the bone 636, and the enamel 638 are displayed in different colors. Alternatively, cross-hatching, different line types and/or different textures may be used to distinguish the different structures.

In addition to natural substructures, computer 24 is programed to detect and display on monitor 34 abnormal conditions such as a filling 640 in molar 626 and decay 642 on molar 628. These abnormal conditions may be indicated in respective colors different from the colors used to indicate the normal tooth substructures. In addition, a circle 644 may be used to highlight a tooth condition, such as decay 642, particularly if the condition is small and possibly undetectable on monitor 34.

As described hereinabove with reference to FIG. 24, computer 24 may display, at the option of the user, many different views of the subject teeth 626 and 628. The views may be elevations or plan views or cross-sections. One or more views may be shown one the same screen at once. The view of the subject tooth or teeth 626, 628 may be a perspective view which is rotating in space, as shown on monitor 34.

Different numbers of teeth may be shown on monitor 34. depending on the preference of the user. One tooth may be selected or even all of the teeth of one or both jaws. In the latter case, the information displayed advantageously includes bite information such as the locations of contact between the occlusal surfaces. Such areas of contact may be highlighted by circles 646 (FIG. 31) or by other means.

Computer 24 is additionally programed to calculate stresses on jaw bones and root structures, depending on the locations of the bite points on the different teeth, the types and sizes of the teeth and statistics as to bite forces. The statistical information may be replaced by measurements of a particular patient's bite.

Another dentitious dimension which may be determined and displayed on monitor 34 is the depth of gingival pockets 648 (FIG. 31). Pantograph data generating device or assembly 26 is particularly adapted to measure pocket depths and collect subgingival data. The pocket depths may be calculated by computer 24 in response to the digitized contour data from pantograph data generating device or assembly 26 and displayed in numerical or other coded form on monitor 34.

As shown in FIG. 1, computer 24 is connected at an input to a voice-recognition unit 650 which in turn receives input signals from an acousto-electric transducer 652, for example, a microphone. Transducer 652 and voice-recognition unit 650 are used by a practitioner to facilitate the input of data into computer 24. Generally, as the practitioner is providing computer with surface data from optical data generating device 22 or pantograph data generating device 26 or X-ray data from X-ray data generating device 28, the practitioner may be vocally identifying the teeth and/or the surfaces to which the surface data or X-ray data pertain. For example, the practitioner might say "tooth number 24, occlusal." In addition, as the dentist identifies a condition or abnormality such as a filling or decay, these characteristics may also be identified to the computer. For example, upon pointing to a particular location with stylus or perio-probe for coordinate output then in conjunction with this data generating device 26, the practitioner will say "decay, tooth number 18, buccal" to facilitate identification of the abnormality by the computer.

These conditions are then depicted on monitor 34 as described hereinabove with reference to FIG. 31. The convenience and facility of vocalization to diagnosis and charting may be readily understood.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for preparing a tooth in a patient's jaw, comprising the steps of:

generating electrically encoded data as to surfaces of said tooth;

transmitting said data to a computer;

operating said computer to generate, on a monitor connected to said computer, a graphic representation of at least one view of said tooth;

selecting an electrically encoded preparation preform from a memory of said computer;

prior to any modification of said tooth, additionally operating said computer to display said electrically encoded preparation preform in overlay as an image on the graphic representation of said one of said views;

only upon completion of said step of additionally operating, using a dental instrument to modify said tooth to assume the shape of said electrically encoded preparation preform;

providing, to said computer, electrical feedback as to motions of said instrument; and modifying said graphic representation in accordance with motions of said instrument to show modifications of said tooth.

2. The method recited in claim 1 wherein said step of operating said computer to generate a graphic representation includes the step of operating said computer to generate, on said monitor, graphic representations of a plurality of views of said tooth.

3. The method recited in claim 2 wherein at least one of said views is generated by said computer upon interpolation of electrically encoded surface data.

4. The method recited in claim 1 wherein said step of generating electrically encoded data includes the step of gathering contour data.

5. The method recited in claim 1 wherein said step of generating electrically encoded data includes the step of producing a video signal.

6. The method recited in claim 1 wherein said step of generating electrically encoded data includes the step of collecting X-ray data as to said tooth.

7. The method recited in claim 1 wherein said view is a cross-sectional view of said tooth.

8. A method for use in forming a preparation in a patient's jaw, comprising the steps of:

generating electrically encoded data specifying pre-existing structure;

transmitting said data to a computer;

operating said computer to generate, on a monitor connected to said computer, a graphic representation of said pre-existing structure;

using a material removal tool to modify said pre-existing structure to form the preparation;

prior to any use of said material removal tool, further operating said computer to predetermine an optimal position and an optimal orientation of said material removal tool with respect to said pre-existing structure; and also prior to any use of said material removal tool, additionally operating said computer to generate, on said monitor, a graphic representation indicating said optimal position and said optimal orientation relative to said pre-existing structure.

9. The method recited in claim 8 wherein said pre-existing structure includes bone in the patient's jaw, said preparation comprising the formation of a bore for receiving an anchor for a dental implant, said optimal position and said optimal orientation being adapted to produce a desired position and a desired orientation of the anchor for the implant.

10. The method recited in claim 9, further comprising the step of also operating said computer to generate, on said monitor, a graphic representation of said anchor in said desired position and said desired orientation relative to said bone and said tooth.

11. The method recited in claim 8 wherein said step of generating electrically encoded data comprises a first step of generating digitized surface data and a second step of generating digitized X-ray data.

12. The method recited in claim 8, further comprising the steps of instructing said computer to modify said optimal position and said optimal orientation and operating said computer to generate, on said monitor, a graphic representation of said tool in the modified position and orientation relative to said pre-existing structure.

13. The method recited in claim 8, further comprising the steps of:

in a practice operation, orienting a dental type instrument in juxtaposition to said pre-existing structure at approximately said optimal position;

providing, to said computer, electrical feedback as to an actual position and an actual orientation of said instrument;

operating said computer to provide feedback to an operator regarding an angle between said optimal orientation and said actual orientation.

14. The method recited in claim 13 wherein said instrument is said tool.

15. The method recited in claim 13 wherein said instrument is a practice instrument having a virtual tip.

16. The method recited in claim 15 wherein said virtual tip is a telescoping member.

17. The method recited in claim 8, further comprising the steps of:

providing, to said computer, electrical feedback as to motions of said tool; and modifying said graphic representation in accordance with motions of said tool to show modifications of said pre-existing structure.

18. The method recited in claim 17, further comprising the step of providing to an operator of said tool an alert signal regarding deviation between an actual position and orientation of said tool during said step of using and said optimal position and said optimal orientation.

19. The method recited in claim 8 wherein said step of further operating said computer to predetermine an optimal position and an optimal orientation of said tool comprises the step of at least partially automatically analyzing said pre-existing structure to determine position and orientation of a desired preparation.

20. The method recited in claim 19 wherein said step of further operating said computer to predetermine an optimal position and an optimal orientation of said tool additionally comprises the steps of:

at least partially automatically accessing an electronic inventory of digitized prosthetic dental devices corresponding to respective actual dental devices of an actual inventory; and at least partially automatically comparing said digitized prosthetic dental devices in different positions and orientations to said pre-existing structure to determine an advantageous position and orientation of a recommended dental device with respect to said pre-existing structure.

21. The method recited in claim 20 wherein said actual dental devices include anchors and angle elements for dental implants.

22. The method recited in claim 8 wherein said step of operating said computer to generate a graphic representation includes the step of operating said computer to generate, on said monitor, graphic representations of a plurality of views of said pre-existing structure.

23. The method recited in claim 22 wherein at least one of said views is generated by said computer upon interpolation of said electrically encoded data.

24. The method recited in claim 8 wherein said step of generating electrically encoded data includes the step of collecting X-ray data as to said pre-existing structure.

25. The method recited in claim 8 wherein said step of generating electrically encoded data includes the step of gathering contour data.

26. The method recited in claim 8 wherein said step of generating electrically encoded data includes the step of producing a video signal.

27. The method recited in claim 8 wherein said step of operating said computer to generate a graphic representation includes the step of operating said computer to generate, on said monitor, graphic representations of a cross-sectional view of said pre-existing structure.

28. A method of preparing for a surgical operation, comprising the steps of:

scanning internal structure in a patient;

digitizing said internal structure in response to said step of scanning;

displaying an image of said internal structure in response to signals produced during said step of digitizing;

providing a practice surgical instrument with a virtual operating tip;

moving said surgical instrument outside of the patient in a simulation of actual surgery on a portion of said internal structure;

automatically monitoring said instrument during said step of moving; and displaying a representation of at least said operating tip of said instrument in overlap with said image of said internal structure during said step of moving.

29. The method recited in claims 28, further comprising the step of establishing a coordinate system reference frame outside of the patient for said internal structure, thereby enabling coordination of said representation with said image.

30. A method for forming a dentitious preparation, comprising the steps of:

displaying on a monitor graphic representation in a first color of three-dimensional structure in a patient's mouth;

also displaying on said monitor, in a second color different from said first color, a graphic representation of desired preparation of said structure, in combination with the graphic representation of said structure;

using a material removal instrument to remove material from a surface of said structure;

additionally displaying on said monitor, in combination with the graphic representation of said structure, a graphic representation of an actual modification of said structure achieved during said step of using, said actual modification being shown in a third color different from said first color and said second color;

calculating a distance between said a first surface defined by said desired preparation and a second surface defined by said actual modification; and selecting said third color from an electronic color palette, wherein different distances are coded by respective colors, said third color corresponding to the calculated distance.

31. The method recited in claim 30 wherein said third color is a predetermined color to indicate a spatial difference between said actual modification and the desired preparation.

32. A method for use in forming a preparation in a patient's jaw, comprising the steps of:

fixing a block of material relative to the patient's jaw so that said block is disposed outside the patient's mouth;

providing a practice dental type instrument with a virtual operating tip;

also providing a material removal tool enslaved to said instrument so that said tool and said instrument move in tandem with one another;

moving said instrument in a virtual operation as if to form the preparation in the patient's jaw;

during said step of moving, automatically operating said tool via the enslavement thereof to said instrument, to form a recess in said block;

providing an actual dental type instrument with an operative material removal tip;

additionally providing a probe enslaved to said actual dental type instrument so that said probe and said actual dental type instrument move in tandem with one another;

upon formation of said recess, operating said actual dental type instrument to form the preparation in the patient's jaw; and during said step of operating, moving said probe inside said recess to thereby guide and limit motion of said actual dental type instrument.

33. A method for use in forming a preparation in a patient's jaw, comprising the steps of:

generating electrically encoded data specifying pre-existing structure;

transmitting said data to a computer;

operating said computer to generate, on a monitor connected to said computer, a graphic representation of said pre-existing structure;

further operating said computer to predetermine an optimal position and an optimal orientation of a material removal tool with respect to said pre-existing structure;

additionally operating said computer to generate, on said monitor, a graphic representation indicating said optimal position and said optimal orientation relative to said pre-existing structure;

instructing said computer to modify said optimal position and said optimal orientation; and operating said computer to generate, on said monitor, a graphic representation of said tool in the modified position and orientation relative to said pre-existing structure.

34. The method recited in claim 33 wherein said step of generating electrically encoded data comprises a first step of generating digitized surface data and a second step of generating digitized X-ray data.

35. A method for use in forming a preparation in a patient's jaw, comprising the steps of:

generating electrically encoded data specifying pre-existing structure;

transmitting said data to a computer;

operating said computer to generate, on a monitor connected to said computer, a graphic representation of said pre-existing structure;

further operating said computer to predetermine an optimal position and an optimal orientation of a material removal tool with respect to said pre-existing structure;

additionally operating said computer to generate, on said monitor, a graphic representation indicating said optimal position and said optimal orientation relative to said pre-existing structure;

in a practice operation, orienting a dental type instrument in juxtaposition to said pre-existing structure at approximately said optimal position;

providing, to said computer, electrical feedback as to an actual position and an actual orientation of said instrument; and operating said computer to provide feedback to an operator regarding an angle between said optimal orientation and said actual orientation.

36. The method recited in claim 35 wherein said instrument is said tool.

37. The method recited in claim 35 wherein said instrument is a practice instrument having a virtual tip.

38. The method recited in claim 37 wherein said virtual tip is a telescoping member.

39. A method for use in forming a preparation in a patient's jaw, comprising the steps of:

generating electrically encoded data specifying pre-existing structure;

transmitting said data to a computer;

operating said computer to generate, on a monitor connected to said computer, a graphic representation of said pre-existing structure;

further operating said computer to predetermine an optimal position and an optimal orientation of a material removal tool with respect to said pre-existing structure;

additionally operating said computer to generate, on said monitor, a graphic representation indicating said optimal position and said optimal orientation relative to said pre-existing structure;

using said tool to modify said pre-existing structure to form the preparation;

providing, to said computer, electrical feedback as to motions of said tool;

modifying said graphic representation in accordance with motions of said tool to show modifications of said pre-existing structure; and providing to an operator of said tool an alert signal regarding deviation between an actual position and orientation of said tool during said step of using and said optimal position and said optimal orientation.

40. A method for use in forming a preparation in a patient's jaw, comprising the steps of:

generating electrically encoded data specifying pre-existing structure;

transmitting said data to a computer;

operating said computer to generate, on a monitor connected to said computer, a graphic representation of said pre-existing structure;

further operating said computer to predetermine an optimal position and an optimal orientation of a material removal tool with respect to said pre-existing structure; and additionally operating said computer to generate, on said monitor, a graphic representation indicating said optimal position and said optimal orientation relative to said pre-existing structure, said step of further operating said computer to predetermine an optimal position and an optimal orientation of said tool comprising the step of at least partially automatically analyzing said pre-existing structure to determine position and orientation of a desired preparation.

41. The method recited in claim 40 wherein said step of further operating said computer to predetermine an optimal position and an optimal orientation of said tool additionally comprises the steps of:

at least partially automatically accessing an electronic inventory of digitized prosthetic dental devices corresponding to respective actual dental devices of an actual inventory; and at least partially automatically comparing said digitized prosthetic dental devices in different positions and orientations to said pre-existing structure to determine an advantageous position and orientation of a recommended dental device with respect to said pre-existing structure.

42. The method recited in claim 41 wherein said actual dental devices include anchors and angle elements for dental implants.

* * * * *